United States Patent
Gross et al.

(10) Patent No.: US 7,300,472 B2
(45) Date of Patent: Nov. 27, 2007

(54) AGENTS FOR COLORING FIBERS CONTAINING KERATIN

(75) Inventors: Wibke Gross, Düsseldorf (DE); Horst Höffkes, Düsseldorf (DE); Doris Oberkobusch, Düsseldorf (DE); Sandra Mausberg, Erkrath (DE)

(73) Assignee: Henkel Kommanditgesellschaft auf Aktien, Dusseldorf (DE)

( * ) Notice: Subject to any disclaimer, the term of this patent is extended or adjusted under 35 U.S.C. 154(b) by 0 days.

(21) Appl. No.: 11/471,219

(22) Filed: Jun. 19, 2006

(65) Prior Publication Data

US 2007/0000074 A1 Jan. 4, 2007

Related U.S. Application Data

(63) Continuation of application No. PCT/EP04/12902, filed on Nov. 13, 2004.

(30) Foreign Application Priority Data

Dec. 19, 2003 (DE) ................ 103 59 831

(51) Int. Cl.
*A61K 7/13* (2006.01)
(52) U.S. Cl. .............. 8/405; 8/406; 8/407; 8/408; 8/411; 8/412; 8/421; 8/570; 8/571; 8/572; 8/573; 8/574; 8/575; 8/576; 548/143; 548/215; 548/262.2; 548/356.1
(58) Field of Classification Search ............ 8/405, 8/406, 407, 408, 411, 412, 421, 570, 571, 8/572, 573, 574, 575, 576; 548/143, 215, 548/262.2, 356.1, 356
See application file for complete search history.

(56) References Cited

U.S. PATENT DOCUMENTS

| | | | |
|---|---|---|---|
| 3,536,436 | A | 10/1970 | Lange et al. |
| 4,931,218 | A | 6/1990 | Schenker et al. |
| 5,061,289 | A | 10/1991 | Clausen et al. |
| 5,294,726 | A | 3/1994 | Behler et al. |
| 5,380,340 | A | 1/1995 | Neunhoeffer et al. |
| 5,534,267 | A | 7/1996 | Neunhoeffer et al. |
| 5,766,576 | A | 6/1998 | Lowe et al. |
| 6,099,592 | A | 8/2000 | Vidal et al. |
| 6,284,003 | B1 | 9/2001 | Rose et al. |
| 6,635,090 | B1 | 10/2003 | Andrean et al. |

FOREIGN PATENT DOCUMENTS

| | | |
|---|---|---|
| DE | 3035056 A1 * | 4/1982 |
| DE | 3723354 | 1/1989 |
| DE | 3843892 | 6/1990 |
| DE | 3926344 | 2/1991 |
| DE | 4133957 | 4/1993 |
| DE | 19543988 | 5/1997 |
| DE | 19856342 | 6/2000 |
| DE | 2359399 | 3/2007 |
| EP | 0743931 | 11/1996 |
| EP | 113975 | 9/2001 |
| EP | 0998909 | 5/2005 |
| GB | 1026978 | 4/1966 |
| GB | 1153196 | 5/1969 |
| JP | 2019576 | 2/1990 |
| WO | 94/08969 | 4/1994 |
| WO | 94/08970 | 4/1994 |
| WO | 96/15765 | 5/1996 |

OTHER PUBLICATIONS

STIC Search Report dated Oct. 20, 2006.*
Kantlehner W. et al.Zur Formylienrung von 2,5 Dialkyl-134-thiadiazolen und 2,3,5-Trialkyl-1,3,4-thiadiazolimsalzen durch Orthoamide der Ameisensaure. Liebigs Ann. Chem, 1982, 2, 298-305 Verlag Chemie GmbJ Weinheim.
Zviak ed. The Science of Hair Care. Dermatology. 1986 235-286. Marcel Dekker, Inc. New York, New York. USA.

* cited by examiner

*Primary Examiner*—Eisa Elhilo
(74) *Attorney, Agent, or Firm*—John S. Child, Jr.

(57) ABSTRACT

The invention relates to agents for coloring fibers containing keratin, in particular, human hair, which comprise selected cationic, CH-acidic heterocycles according to formula I

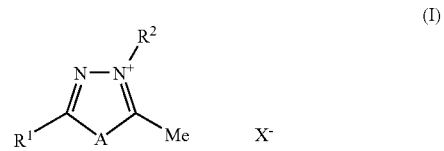

(I)

in which A, $R^1$, $R^2$ and $X^-$ are as defined in the application, in combination with reactive carbonyl compounds, to the use of this combination in agents for coloring fibers containing keratin, for freshening up the color or nuancing fibers containing keratin which have already been colored, and to a method of coloring fibers containing keratin, in particular, human hair.

33 Claims, No Drawings

AGENTS FOR COLORING FIBERS CONTAINING KERATIN

CROSS-REFERENCE TO RELATED APPLICATIONS

This application is a continuation under 35 U.S.C. §365 (c) and 35 U.S.C. §120 of International Application PCT/EP2004/012902, filed Nov. 13, 2004. This application also claims German priority under 35 U.S.C. §119 of Application 103 59 831.6, filed Dec. 19, 2003. Each application is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION (1) Field of the Invention

The invention relates to an agent for coloring fibers containing keratin, in particular, human hair, which comprises selected cationic, CH-acidic heterocycles in combination with reactive carbonyl compounds, to the use of this combination in agents for coloring fibers containing keratin, for freshening up the color or nuancing of fibers containing keratin which have already been colored, and to a method of coloring fibers containing keratin, in particular, human hair.

For coloring fibers containing keratin, either direct dyes or oxidation dyes, which arise as a result of oxidative coupling of one or more developer components with one another or with one or more coupler components, are generally used. Coupler and developer components are also referred to as oxidation dye precursors.

The developer components used are usually primary aromatic amines with a further free or substituted hydroxy or amino group located in the para or ortho position, diaminopyridine derivatives, heterocyclic hydrazones, 4-aminopyrazolone derivatives, and 2,4,5,6-tetraaminopyrimidine and derivatives thereof.

Specific representatives are, for example, p-phenylenediamine, p-tolylenediamine, 2,4,5,6-tetraaminopyrimidine, p-aminophenol, N,N-bis(2-hydroxyethyl)-p-phenylenediamine, 2-(2,5-diaminophenyl)ethanol, 2-(2,5-diaminophenoxy)ethanol, 1-phenyl-3-carboxyamido-4-aminopyrazol-5-one, 4-amino-3-methylphenol, 2-aminomethyl-4-aminophenol, 2-hydroxymethyl-4-aminophenol, 2-hydroxy-4,5,6-triaminopyrimidine, 2,4-dihydroxy-5,6-diaminopyrimidine and 2,5,6-triamino-4-hydroxypyrimidine.

The coupler components used as usually m-phenylenediamine derivatives, naphthols, resorcinol and resorcinol derivatives, pyrazolones, m-aminophenols and substituted pyridine derivatives. Suitable coupler substances are, in particular, α-naphthol, 1,5-, 2-7- and 1,7-dihydroxynaphthalene, 5-amino-2-methylphenol, m-aminophenol, resorcinol, resorcinol monomethyl ether, m-phenylenediamine, 2,4-diaminophenoxyethanol, 2-amino-4-(2-hydroxyethylamino) anisole (Lehmann's Blue), 1-phenyl-3-methylpyrazol-5-one, 2,4-dichloro-3-aminophenol, 1,3-bis(2,4-diaminophenoxy)propane, 2-chlororesorcinol, 4-chlororesorcinol, 2-chloro-6-methyl-3-aminophenol, 2-methylresorcinol, 5-methylresorcinol, 3-amino-6-methoxy-2-methylaminopyridine and 3,5-diamino-2,6-dimethoxypyridine.

With regard to further customary dye components, reference is made expressly to the "Dermatology" series, published by Ch. Culnan, H. Maibach, Verlag Marcel Dekker Inc., New York, Basle, 1986, vol. 7, Ch. Zviak, The Science of Hair Care, chapter 7, pages 248–250 (Direct Dyes) and chapter 8, pages 264–267 (Oxidation Dyes), and the "European Inventory of Cosmetic Raw Materials", 1996, published by the European Commission, obtainable in disk from the Bundesverband der deutschen Industrie- und Handelsunternehmen für Arzneimittel, Reformwaren und Körperpflegemittel e.V., Mannheim, Bezug genommen.

With oxidation dyes, although it is possible to achieve intense colorations with good fastness properties, the development of the color takes place, however, inter alia under the influence of oxidizing agents such as, for example, $H_2O_2$, which in some cases can result in damage to the fibers. The provision of oxidation hair colorations with adequate fastness properties, in particular, with very good wash-, light- and rubbing-fastnesses, continues to be problematic.

Furthermore, some oxidation dye precursors or certain mixtures of oxidation dye precursors can sometimes have a sensitizing effect in people with sensitive skin. Direct dyes are applied under more gentle conditions, but their disadvantage is that the colorations often only have inadequate fastness properties.

Colorants comprising cationic, CH-acidic heterocycles according to formula (I) below, and the use thereof for coloring fibers containing keratin or for freshening up the color or nuancing fibers containing keratin which have already been colored are not known to date.

(2) Description of Related Art, Including Information Disclosed Under 37 C.F.R. §§ 1.97 and 1.98

The publication U.S. Pat. No. 3,855,210 proposes an improved process for the preparation of photosensitive styryl dyes with various heterocyclic head groups. The use of these dyes and their precursor compounds in agents for coloring fibers containing keratin is not described.

BRIEF SUMMARY OF THE INVENTION

It is an object of the present invention to provide colorants for fibers containing keratin, in particular, human hair, which, with regard to color depth, gray coverage and fastness properties, such as, for example, light-, rubbing- and washing-fastness, and also perspiration- and cold-wave-fastness, are at least qualitatively equivalent to customary oxidation hair colorants, but without necessarily relying on oxidizing agents such as, for example, $H_2O_2$. Moreover, the colorants must have no or only a very slight sensitization potential.

Surprisingly, it has now been found that the compounds shown in formula I, in particular, in combination with compounds containing at least one reactive carbonyl group, are exceptionally suitable for coloring fibers containing keratin even in the absence of oxidizing agents. They produce colorations with excellent brilliance and color depth and lead to diverse color nuances. In particular, colorations with improved fastness properties, in particular, improved light-fastness, over a nuance range from yellow via yellow-brown, orange, brown-orange, brown, red and red-violet are obtained. The use of oxidizing agents, however, should not be excluded in principle.

The invention provides an agent for coloring fibers containing keratin, in particular, human hair, comprising, as component A, at least one compound according to formula I and/or enamine form thereof,

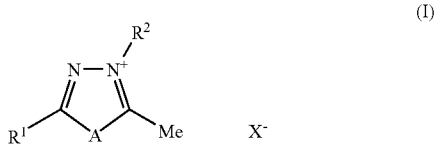

where
R$^1$ is a hydrogen atom, a hydroxy group, a mercapto group, a linear or cyclic C$_1$–C$_6$-alkyl group, a C$_2$–C$_6$-alkenyl group, an optionally substituted aryl group, an optionally substituted heteroaryl group, an aryl-C$_1$–C$_6$-alkyl group, a C$_1$–C$_6$-hydroxyalkyl group, a C$_2$–C$_6$-polyhydroxyalkyl group, a C$_1$–C$_6$-alkoxy-C$_2$–C$_6$-alkyl group, a C$_1$–C$_6$-sulfoalkyl group, a C$_1$–C$_6$-carboxyalkyl group, a group R$^I$R$^{II}$N—(CH$_2$)$_m$-, in which R$^I$ and R$^{II}$, independently of one another, are a hydrogen atom, a linear or cyclic C$_1$–C$_6$-alkyl group, a C$_2$–C$_6$-alkenyl group, a C$_1$–C$_6$-hydroxyalkyl group or an aryl-C$_1$–C$_6$-alkyl group, where R$^I$ and R$^{II}$, together with the nitrogen atom, can form a 5-, 6- or 7-membered ring and m is a number 0, 1, 2, 3 or 4, R$^2$ is a linear or cyclic C$_1$–C$_6$-alkyl group, a C$_2$–C$_6$-alkenyl group, an optionally substituted aryl group, an optionally substituted heteroaryl group, an aryl-C$_1$–C$_6$-alkyl group, a C$_1$–C$_6$-hydroxyalkyl group, a C$_2$–C$_6$-polyhydroxyalkyl group, a C$_1$–C$_6$-sulfoalkyl group, a C$_1$–C$_6$-carboxyalkyl group, a group R$^{III}$R$^{IV}$N—(CH$_2$)$_q$-, in which R$^{III}$ and R$^{IV}$, independently of one another, are a hydrogen atom, a linear or cyclic C$_1$–C$_6$-alkyl group, a C$_2$–C$_6$-alkenyl group, a C$_1$–C$_6$-hydroxyalkyl group or an aryl-C$_1$–C$_6$-alkyl group and q is a number 1, 2, 3 or 4, A is an oxygen atom, a sulfur atom or a group N—R, in which R is a hydrogen atom, a linear or cyclic C$_1$–C$_6$-alkyl group, a C$_2$–C$_6$-alkenyl group, a C$_1$–C$_6$-hydroxyalkyl group or an aryl-C$_1$–C$_6$-alkyl group, X$^-$ is a physiologically compatible anion, and, as component B, at least one compound with a reactive carbonyl group.

BRIEF DESCRIPTION OF THE SEVERAL VIEWS OF THE DRAWING(S)

Not Applicable

DETAILED DESCRIPTION OF THE INVENTION

The radical R$^1$ is preferably a C$_1$–C$_6$-alkyl group, in particular, a methyl group.

The radical R$^2$ is preferably a C$_1$–C$_6$-alkyl group, a C$_1$–C$_6$-hydroxyalkyl group or a C$_2$–C$_6$-alkenyl group, in particular, a methyl group, ethyl group, 2-propenyl group or 2-hydroxyethyl group.

If, in the compound according to the invention according to formula I, the group A is a group N—R, this compound is referred to as 5-methyl-4H-1,2,4-triazolium derivative with the radical R$^1$ in position 3 of the heterocyclic five-membered ring. In a preferred embodiment of the invention, A is an oxygen atom (2-methyl-1,3,4-oxadiazolium derivatives; R$^1$ in 5 position) or a sulfur atom (2-methyl-1,3,4-thiadiazolium derivatives; R$^1$ in 5 position), A is particularly preferably a sulfur atom.

The physiologically compatible anions are preferably selected from halide, benzenesulfonate, p-toluenesulfonate, C$_1$–C$_4$-alkanesulfonate, trifluoromethanesulfonate, perchlorate, 0.5 sulfate, hydrogensulfate, tetrafluoroborate, hexafluorophosphate or tetrachlorozincate. X$^-$ is particularly preferably a halide, in particular, chloride, bromide or iodide, p-toluenesulfonate, tetrafluoroborate, trifluoromethanesulfonate, hexafluorophosphate, 0.5 sulfate, or hydrogensulfate. The anions tetrafluoroborate, chloride, bromide, iodide, hydrogensulfate or p-toluenesulfonate are particularly preferably used as X$^-$.

Preferably, the compounds according to formula I are selected from the group consisting of 2-methyl-5-phenyl-3-(phenylmethyl)-1,3,4-thiadiazolium tetrafluoroborate, 2-methyl-5-phenyl-3-(phenylmethyl)-1,3,4-thiadiazolium p-toluenesulfonate, 5-(4-chlorophenyl)-2-methyl-3-phenyl-1,3,4-thiadiazolium tetrafluoroborate, 2-methyl-3-(4-nitrophenyl)-5-phenyl-1,3,4-thiadiazolium tetrafluoroborate, 2,3-dimethyl-5-phenyl-1,3,4-thiadiazolium tetrafluoroborate, 2,3-dimethyl-5-phenyl-1,3,4-thiadiazolium p-toluenesulfonate, 2,5-dimethyl-3-(phenylmethyl)-1,3,4-thiadiazolium bromide, 2,5-dimethyl-3-(phenylmethyl)-1,3,4-thiadiazolium chloride, 2,5-dimethyl-3-hexyl-1,3,4-thiadiazolium iodide, 2,5-dimethyl-3-(2-propenyl)-1,3,4-thiadiazolium bromide, 2,5-dimethyl-3-(2-propenyl)-1,3,4-thiadiazolium tetrafluoroborate, 2,5-dimethyl-3-(2-propenyl)-1,3,4-thiadiazolium p-toluenesulfonate, 3-ethyl-2,5-dimethyl-1,3,4-thiadiazolium bromide, 3-ethyl-2,5-dimethyl-1,3,4-thiadiazolium tetrafluoroborate, 3-ethyl-2,5-dimethyl-1,3,4-thiadiazolium p-toluenesulfonate, 2,5-dimethyl-3-(2-hydroxyethyl)-1,3,4-thiadiazolium bromide, 2,5-dimethyl-3-(2-hydroxyethyl)-1,3,4-thiadiazolium p-toluenesulfonate, 3-ethyl-5-(4-methoxyphenyl)-2-methyl-1,3,4-oxadiazolium iodide, 3-ethyl-2-methyl-5-phenyl-1,3,4-oxadiazolium iodide, 3-ethyl-2-methyl-5-phenyl-1,3,4-oxadiazolium tetrafluoroborate, 2,3-dimethyl-5-phenyl-1,3,4-oxadiazolium tetrafluoroborate, 4,5-dimethyl-1,3-diphenyl-4H-1,2,4-triazolium chloride, 4-ethyl-5-methyl-1,3-diphenyl-4H-1,2,4-triazolium chloride and 4-ethyl-5-methyl-1,3-diphenyl-4H-1,2,4-triazolium p-toluenesulfonate.

The compounds according to the invention according to formula I of component A are very particularly preferably selected from 2,5-dimethyl-3-(2-propenyl)-1,3,4-thiadiazolium bromide, 2,5-dimethyl-3-(2-propenyl)-1,3,4-thiadiazolium tetrafluoroborate, 2,5-dimethyl-3-(2-propenyl)-1,3,4-thiadiazolium p-toluenesulfonate, 3-ethyl-2,5-dimethyl-1,3,4-thiadiazolium bromide, 3-ethyl-2,5-dimethyl-1,3,4-thiadiazolium tetrafluoroborate and 3-ethyl-2,5-dimethyl-1,3,4-thiadiazolium p-toluenesulfonate.

Examples of the groups and radicals specified as substituents within the scope of this application will be mentioned below. Examples of C$_1$–C$_6$-alkyl groups are the groups methyl, ethyl, propyl, isopropyl, n-butyl, sec-butyl and tert-butyl, n-pentyl and n-hexyl. Propyl, ethyl and methyl are preferred alkyl groups. Examples of corresponding cyclic alkyl groups are cyclopentyl and cyclohexyl. Examples of preferred C$_2$–C$_6$-alkenyl groups are vinyl and 2-propenyl (allyl). C$_1$–C$_6$-Alkoxy groups preferred according to the invention are, for example, a methoxy group or an ethoxy group. The methoxycarbonyl group, ethoxycarbonyl group, n-propoxycarbonyl group, isopropoxycarbonyl group, n-butoxycarbonyl group, sec-butoxycarbonyl group and tert-butoxycarbonyl group are examples of $C_1$–$C_4$-alkoxycarbonyl groups; the methoxycarbonyl group and the ethoxycarbonyl group are particularly preferred here. In addition, preferred examples of a $C_1$–$C_6$-hydroxyalkyl group which may be mentioned are a hydroxymethyl group, a 2-hydroxyethyl group, a 2-hydroxypropyl group, a 3-hydroxypropyl group, a 4-hydroxybutyl group, a 5-hydroxypentyl group and a 6-hydroxyhexyl group. A 2-hydroxyethyl group is particularly preferred. The methoxyethyl group, ethoxyethyl group, methoxypropyl group, methoxybutyl group, ethoxybutyl group and the methoxyhexyl group are examples of $C_1$–$C_6$-alkoxy-$C_2$–$C_6$-alkyl groups according to the invention. Examples of a $C_2$–$C_6$-polyhydroxyalkyl group are the 2,3-dihydroxypropyl group, 3,4-dihydroxybutyl group and the 2,4-dihydroxybutyl group. A preferred hydroxy-$C_1$–$C_6$-alkoxy group is the 2-hydroxyethoxy group. Preferred aryl groups are phenyl, naphthyl and biphenyl. Examples of a heteroaryl group are pyrrolidyl, 2-furyl, 2-thienyl, 4-pyridyl, 3-pyridyl, 2-pyridyl, triazolyl and 1-imidazolyl. Examples of a heterocycle-$C_{1-4}$-alkyl group are pyrrolidino-($C_{1-4}$)-alkyl, pipieridino-($C_{1-4}$)-alkyl, morpholino-($C_{1-4}$)-alkyl, 2-furyl-($C_{1-4}$)-alkyl, 2-thienyl-($C_{1-4}$)-alkyl, 4-pyridyl-($C_{1-4}$)-alkyl, 3-pyridyl-($C_{1-4}$)-alkyl, 2-pyridyl-($C_{1-4}$)-alkyl, triazolyl-($C_{1-4}$)-alkyl and 1-imidazolyl-($C_{1-4}$)-alkyl. The aryl groups and the heteroaryl groups are optionally substituted, preferably by one or more groups which are selected from a halogen atom, a hydroxy group, an amino group, a $C_1$–$C_6$-alkoxy group, a $C_1$–$C_6$-alkyl group, a nitro group, a carboxy group, a carboxamido group and a cyano group. Examples of halogen atoms are F, Cl, Br or I atoms, with Cl atoms being very particularly preferred. Preferred $C_1$–$C_6$-aminoalkyl groups are the aminomethyl group, the aminoethyl group and the aminopropyl group. Preferred aryl-$C_1$–$C_6$-alkyl groups are phenylmethyl (benzyl) and 2-phenylethyl. The aminomethyl group, 2-aminoethyl group, 3-aminopropyl group, 2-dimethylaminoethyl group, diethylaminomethyl group, dimethylaminomethyl group, 2-methylaminoethyl group, dimethylamino group, piperidinomethyl group, pyrrolidinomethyl group, morpholinomethyl group and the amino group are examples of a group R'R"N—$(CH_2)_n$—, where the diethylaminomethyl group, piperidinomethyl, 2-dimethylaminoethyl group, dimethylamino group and the amino group are particularly preferred. A preferred $C_1$–$C_6$-carboxyalkyl group is the 3-carboxypropyl group. Particularly preferred $C_2$–$C_6$-alkenylene groups are vinylene and propylene. A particularly preferred $C_4$–$C_6$-alkadienylene group is the 1,3-butadiene-1,4-diyl group. The groups 1-carboxypropylene and 1-carboxyethylene are preferred carboxy-($C_1$–$C_4$)-alkylene groups. According to the invention, the other terms used are derived from the definitions given here.

The compounds according to the invention according to formula I are CH-acidic compounds. They are present in solution in chemical equilibrium with the enamine form of the compounds according to formula I. With the help of a base, it is possible, starting from the compounds according to formula I, to synthesize the corresponding enamines in a targeted manner by deprotonation at the methyl radical adjacent to the quaternized nitrogen atom. By way of example, this deprotonation is illustrated below. A compound according to the formula Ia is an example of the enamine form according to the invention of the compounds according to formula I.

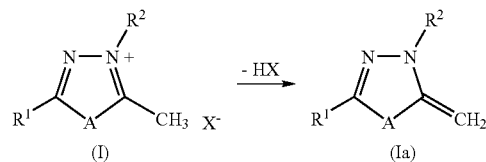

Fibers containing keratin are understood as meaning wool, furs, feathers and, in particular, human hair. The colorants according to the invention can in principle, however, also be used for coloring other natural fibers, such as, for example, cotton, jute, sisal, linen or silk, modified natural fibers, such as, for example, regenerated cellulose, nitrocellulose, alkylcellulose or hydroxyalkylcellulose or acetylcellulose.

Compounds of the formula I are for the most part known in the literature, commercially available or preparable by known synthesis methods according to W. Kantlehner et al., *Liebigs Ann. Chem.*, 1982, 2, 298–305; R. Grashey et al., *Chem.-Ztg.*, 1985, 109(10), 350–351.

Colorations with increased brilliance and improved fastness properties (light-fastness, wash-fastness, rubbing-fastness) over a wide nuance range are achieved if the compounds of the formula I used are present according to the invention together with at least one substance with a reactive carbonyl group (also called component B or reactive carbonyl compound below) in the agents according to the invention. Reactive carbonyl compounds according to the invention have at least one carbonyl group as reactive group which reacts with the CH-acidic compound according to formula I to form a carbon-carbon bond. In addition, according to the invention it is also possible to use those compounds as component B in which the reactive carbonyl group is derivatized or masked in such a way that the reactivity of the carbon atom of the derivatized carbonyl group toward the CH-acidic compounds of the formula I is always present. These derivatives are preferably addition compounds:

a) of amines and derivatives thereof with the formation of imines or oximes as addition compound
b) of alcohols with the formation of acetals or ketals as addition compound
c) of water with the formation of hydrates as addition compound (component B is derived in this case c) from an aldehyde ab)

onto the carbon atom of the carbonyl group of the reactive carbonyl compound.

Component B is preferably selected from compounds according to formula II,

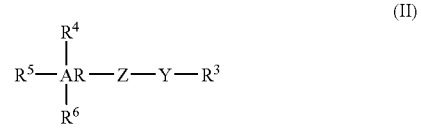

where
AR is benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, cinnoline, acridine, julolidine, acenaphthene, fluorene, biphenyl, diphenylmethane, benzophenone, diphenyl ether, azobenzene, chromone, coumarin, diphenylamine, stilbene, where the N-heteroaromatics may also be quaternized, $R^3$ is a hydrogen atom, a $C_1$–$C_6$-alkyl group, $C_2$–$C_6$-acyl group, $C_2$–$C_6$-alkenyl group, $C_1$–$C_4$-perfluoroalkyl group, an optionally substituted aryl or heteroaryl group, $R^4$, $R^5$ and $R^6$, independently of one another, are a hydrogen atom, a halogen atom, a $C_1$–$C_6$-alkyl group, $C_1$–$C_6$-alkoxy group, $C_1$–$C_6$-aminoalkyl group, $C_1$–$C_6$-hydroxyalkyl group, a $C_1$–$C_6$-alkoxy-$C_1$–$C_6$-alkyloxy group, a $C_2$–$C_6$-acyl group, an acetyl group, carboxyl group, carboxylato group, carbamoyl group, sulfo group, sulfato group, sulfonamide group, sulfonamido group, $C_2$–$C_6$-alkenyl group, an aryl group, an aryl-$C_1$–$C_6$-alkyl group, a hydroxy group, a nitro group, a pyrrolidino group, a morpholino group, a piperidino group, an amino group or ammonio group or a 1-imidazol(in)io group, where the last three groups can be substituted by one or more $C_1$–$C_6$-alkyl groups, $C_1$–$C_6$-carboxyalkyl groups, $C_1$–$C_6$-hydroxyalkyl groups, $C_2$–$C_6$-alkenyl groups, $C_1$–$C_6$-alkoxy-$C_1$–$C_6$-alkyl groups, by optionally substituted benzyl groups, by sulfo-($C_1$–$C_4$)-alkyl groups or heterocycle-($C_1$–$C_4$)-alkyl groups, where two of the radicals from $R^4$, $R^5$, $R^6$ and -Z-Y—$R^3$, together with the remainder of the radical, can also form a fused-on optionally substituted 5-, 6- or 7-membered ring, which can likewise carry a fused-on aromatic ring, where the system AR can, depending on the size of the ring, carry further substituents which, independently of one another, can be the same groups as $R^4$, $R^5$ and $R^6$, Z is a direct bond, a carbonyl group, a carboxy-($C_1$–$C_4$)-alkylene group, an optionally substituted $C_2$–$C_6$-alkenylene group, $C_4$–$C_6$-alkadienylene group, furylene group, thienylene group, arylene group, vinylene-arylene group, vinylenefurylene group, vinylenethienylene group, where Z, together with the —Y—$R^3$ group, can also form an optionally substituted 5-, 6- or 7-membered ring, Y is a group which is selected from carbonyl, a group according to formula III and a group according to formula IV, $$\begin{matrix} \diagdown \\ C=N-R^7 \\ \diagup \end{matrix}$$ (III)

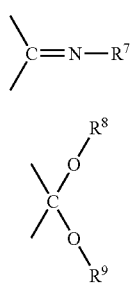 (IV)

where
$R^7$ is a hydrogen atom, a hydroxy group, a $C_1$–$C_4$-alkoxy group, a $C_1$–$C_6$-alkyl group, a $C_1$–$C_6$-hydroxyalkyl group, a $C_2$–$C_6$-polyhydroxyalkyl group, a $C_1$–$C_6$-alkoxy-$C_1$–$C_6$-alkyl group, $R^8$ and $R^9$, independently of one another, are a hydrogen atom, a $C_1$–$C_6$-alkyl group, an aryl group or jointly form, together with the structural element O—C—O of the formula IV, a 5- or 6-membered ring.

Component B is particularly preferably selected from the group consisting of acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxyacetophenone diethyl ketal, 4-hydroxy-3-methoxyacetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromoacetophenone, 4-hydroxy-3-nitroacetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxybenzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4,5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,4-dihydroxy-5-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 3,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde, piperonal, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline (Fischers aldehyde or tribase aldehyde), 2-indolealdehyde, 3-indolealdehyde, 1-methylindole-3-aldehyde, 2-methylindole-3-aldehyde, 1-acetylindole-3-aldehyde, 3-acetylindole, 1-methyl-3-acetylindole, 2-(1',3',3'-trimethyl-2-indolinylidene)acetaldehyde, 1-methylpyrrole-2-aldehyde, 1-methyl-2-acetylpyrrole, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-thenoyltrifluoroacetone, chromone-3-aldehyde, 3-(5'-nitro-2'-furyl)acrolein, 3-(2'-furyl)acrolein and imidazole-2-aldehyde, 1,3-diacetylbenzene, 1,4-diacetylbenzene, 1,3,5-triacetylbenzene, 2-benzoylacetophenone, 2-(4'-methoxybenzoyl)acetophenone, 2-(2'-furoyl)acetophenone, 2-(2'-pyridoyl)acetophenone and 2-(3'-pyridoyl)acetophenone, benzylidene acetone, 4-hydroxybenzylidene acetone, 2-hydroxybenzylidene acetone, 4-methoxybenzylidene acetone, 4-hydroxy-3-methoxybenzylidene acetone, 4-dimethylaminobenzylidene acetone, 3,4-methylenedioxybenzylidene acetone, 4-pyrrolidinobenzylidene acetone, 4-piperidinobenzylidene acetone, 4-morpholinobenzylidene acetone, 4-diethylaminobenzylidene acetone, 3-benzylidene-2,4-pentanedione, 3-(4'-hydroxybenzylidene)-2,4-pentanedione, 3-(4'-dimethylaminobenzylidene)-2,4-pentanedione, 2-benzylidenecyclohexanone, 2-(4'-hydroxybenzylidene)cyclohexanone, 2-(4'-dimethylaminobenzylidene)cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)cyclopentanone, 2-(4'-dimethylaminobenzylidene)cyclopentanone, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal, 5-(4-morpholinophenyl)penta-2,4-dienal, 5-(4-pyrrolidinophenyl)penta-2,4-dienal, 6-(4-dimethylaminophenyl)hexa-3,5-dien-2-one, 6-(4-diethylaminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-nitro-1-naphthaldehyde, 2-nitrocinnamaldehyde, 3-nitrocinnamaldehyde, 4-nitrocinnamaldehyde, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 4-acetyl-1-methylpyridinium, 2-acetyl-1-methylpyridinium, 4-acetyl-1-methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium, 5-acetyl-1-methylquinolinium, 6-acetyl-1-methylquinolinium, 7-acetyl-1-methylquinolinium, 8-acetyl-1-methylquinolinium, 5-acetyl-1-ethylquinolinium, 6-acetyl-1-ethylquinolinium, 7-acetyl-1-ethylquinolinium, 8-acetyl-1-ethylquinolinium, 5-acetyl-1-benzylquinolinium, 6-acetyl-1-benzylquinolinium, 7-acetyl-1-benzylquinolinium, 8-acetyl-1-benzylquinolinium, 5-acetyl-1-allylquinolinium, 6-acetyl-1-allylquinolinium, 7-acetyl-1-allylquinolinium and 8-acetyl-1-allylquinolinium, 9-formyl-10-methylacridinium, 4-(2'-formylvinyl)-1-methylpyridinium, 1,3-dimethyl-2-(4'-formylphenyl)benzimidazolium, 1,3-dimethyl-2-(4'-formylphenyl)imidazolium, 2-(4'-formylphenyl)-3-methylbenzothiazolium, 2-(4'-acetylphenyl)-3-methylbenzothiazolium, 2-(4'-formylphenyl)-3-methylbenzoxazolium, 2-(5'-formyl-2'-furyl)-3-methylbenzothiazolium, 2-(5'-formyl-2'-furyl)-3-methylbenzothiazolium, 2-(5'-formyl-2'-thienyl)-3-methylbenzothiazolium, 2-(3'-formylphenyl)-3-methylbenzothiazolium, 2-(4'-formyl-1-naphthyl)-3-methylbenzothiazolium, 5-chloro-2-(4'-formylphenyl)-3-methylbenzothiazolium, 2-(4'-formylphenyl)-3,5-dimethylbenzothiazolium benzenesulfonate, p-toluenesulfonate, methanesulfonate, perchlorate, sulfate, chloride, bromide, iodide, tetrachlorozincate, methylsulfate, trifluoromethanesulfonate, tetrafluoroborate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, and any mixtures of the above compounds.

In a specific embodiment, it may be favorable to choose component B such that the group Y from formula II is not a carbonyl group. In this case, it may be preferred to choose component B from 2-{[(2-hydroxyethyl)imino]methyl}phenol, 3{[(2-hydroxyethyl)imino]methyl}phenol, 4-{[(2-hydroxyethyl)imino]methyl}phenol, 3{[(2-hydroxyethyl)imino]methyl}benzene-1,2-diol, 4{[(2-hydroxyethyl)imino]methyl}benzene-1,3-diol, 2{[(2-hydroxyethyl)imino]methyl}benzene-1,4-diol, 2-{[(2-hydroxyethyl)imino]methyl}benzene-1,3-diol, 4{[(2-hydoxyethyl)imino]methyl}benzene-1,2-diol, 5-{[(2-hydroxyethyl)imino]methyl}benzene-1,3-diol, 4-{[(2-hydroxyethyl)imino]methyl}benzene-1,2,3-triol, 6-{[(2-hydroxyethyl)imino]methyl}benzene-1,2,4-triol, 3-{[(2-hydroxyethyl)imino]methyl}benzene-1,2,4-triol, 2-{[(2-hydroxyethyi)imino]methyl}benzene-1,3,5-triol, 5-{[(2-hydroxyethyl)imino]methyl}benzene-1,2,4-triol, 3-{[(2-hydroxyethyl)imino]methyl}benzene-1,2,4-triol, 2-{[(2-methoxyphenyl)methylene]amino}ethanol, 2-{[(3-methoxyphenyl)methylene]amino}ethanol, 2-{[(4-methoxyphenyl)methylene]amino}ethanol, 2-{[(2-ethoxyphenyl)methylene]amino}ethanol, 2-{[(3-ethoxyphenyl)methylene]amino}ethanol, 2-{[(4-ethoxyphenyl)methylene]amino}ethanol, 2-{[(2,3-dimethoxyphenyl)methylene]amino}ethanol, 2-{[(2,4-dimethoxyphenyl)methylene]amino}ethanol, 2-{[(2,5-dimethoxyphenyl)methylene]amino}ethanol, 2-{[(2,6-dimethoxyphenyl)methylene]amino}ethanol, 2-{[(3,4-dimethoxyphenyl)methylene]amino}ethanol, 2-{[(3,5-dimethoxyphenyl)methylene]amino}ethanol, 2-{[(2,3,4-trimethoxyphenyl)methylene]amino}ethanol, 2-{[(2,3,5-trimethoxyphenyl)methylene]amino}ethanol, 2-{[(2,3,6-trimethoxyphenyl)methylene]amino}ethanol, 2-{[(2,4,6-trimethoxyphenyl)methylene]amino}ethanol, 2-{[(2,4,5-trimethoxyphenyl)methylene]amino}ethanol, 2-{[(2,3,6-trimethoxyphenyl)methylene]amino}ethanol, 4-{[(2-hydroxyethyl)imino]methyl}-3-methoxyphenol, 4-{[(2-hydroxyethyl)imino]methyl}-3-methoxyphenol, 4-{[(2-hydroxyethyl)imino]methyl}-2-methoxyphenol, 5-{[(2-hydroxyethyl)imino]methyl}-2-methoxyphenol, 2-{[(2-hydroxyethyl)imino]methyl}-5-methoxyphenol, 3-ethoxy-4-{[(2-hydroxyethyl)imino]methyl}phenol, 2-ethoxy-4-{[(2-hydroxyethyl)imino]methyl}phenol, 5-ethoxy-2-{[(2-hydroxyethyl)imino]methyl}phenol, 2-ethoxy-5-{[(2-hydroxyethyl)imino]methyl}phenol, 4-{[(2-hydroxyethyl)imino]methyl}-2,3-dimethoxyphenol, 4-{[(2-hydroxyethyl)imino]methyl}-2,5-dimethoxyphenol, 4-{[(2-hydroxyethyl)imino]methyl}-3,5-dimethoxyphenol, 4-{[(2-hydroxyethyl)imino]methyl}-2,6-dimethoxyphenol, 2,6-diethoxy-4-{[(2-hydroxyethyl)imino]methyl}phenol, 3,5-diethoxy-4-{[(2-hydroxyethyl)imino]-methyl}phenol, 4-{[(2-hydroxyethyl)imino]methyl}-3-methylphenol, 4-{[(2-hydroxyethyl)imino]methyl}-2-methylphenol, 4-{[(2-hydroxyethyl)imino]methyl}-2,3-dimethylphenol, 4-{[(2-hydroxyethyl)imino]methyl}-2,5-dimethylphenol, 4-{[(2-hydroxyethyl)imino]methyl}-3,5-dimethylphenol, 4-{[(2-hydroxyethyl)imino]methyl}-2,6-dimethylphenol, 2-({[4-(dibutylamino)phenyl]methylene}amino)ethanol, 2({[2-chloro-4-dimethylamino)phenyl]methylene}amino)ethanol, 2-({[4-dimethylamino)-2-methylphenyl]methylene}amino)ethanol, 2-({[4-(dimethylamino)-2-methoxyphenyl]methylene}-amino) ethanol, 2-({[2-dimethylamino)phenyl]methylene}amino) ethanol, 2-({[4-(dimethylamino)phenyl]methylene}amino) ethanol, 2-({[4-(diethylamino)phenyl]methylene}amino) ethanol, 5-(dimethylamino)-2-{[(2-hydroxyethyl)imino]methyl}phenol, 5-(diethylamino)-2-{[2-hydroxyethyl)imino]methyl}phenol, 2-{[(4-pyrrolidine-1-ylphenyl)methylene]amino}ethanol, 2-{[(4-piperidin-1-ylphenyl)methylene]amino}ethanol, 2-{[(4-morpholin-4-ylphenyl)methylene]amino}ethanol, 2-{[(2-morpholin-4-ylphenyl)methylene]amino}ethanol, 2-{[(2-methoxy-1-naphthyl)methylene]amino}ethanol, 2-{[(4-methoxy-1-naphthyl)methylene]amino}ethanol, 1-{[(2-hydroxyethyl)imino]methyl}-2-naphthol, 4-{[(2-hydroxyethyl)imino]methyl}-1-naphthol, 4-{[(2-hydroxyethyl)imino]methyl}naphthalene-1,3-diol, 4-{[(2-hydroxyethyl)imino]methyl}-2-methoxy-1-naphthol, 1-{[(2-hydroxyethyl)imino]methyl}-4-methoxy-2-naphthol, 4-{[(2-hydroxyethyl)imino]methyl}-1-methoxy-2-naphthol, 2-{[(2,4-dimethoxy-1-naphthyl)methylene]amino}ethanol, 2-{[(3,4-dimethoxy-1-naphthyl)methylene]amino}ethanol, 2-({[4-(dimethylamino)-1-naphthyl]methylene}amino)ethanol, 2-({3-[4-(dimethylamino)phenyl]prop-2-enylidene}amino)ethanol, 2-({3-[4-diethylamino)phenyl]prop-2-enylidene}amino) ethanol, 4-{3-[(2-hydroxyethyl)imino]prop-1-enyl}-2-methoxyphenol, 2-(diethoxymethyl)phenol, 3-(diethoxymethyl)phenol, 4-(diethoxymethyl)phenol, 3-(diethoxymethyl)benzene-1,2-diol, 4-(diethoxymethyl)benzene-1,3-diol, 2-(diethoxymethyl)benzene-1,4-diol, 2-(diethoxymethyl)benzene-1,3-diol, 4-(diethoxymethyl)benzene-1,2-diol, 5-(diethoxymethyl)benzene-1,3-diol, 4-(diethoxymethyl)benzene-1,2,3-triol, 6-(diethoxymethyl)benzene-1,2,4-triol, 3-(diethoxymethyl)benzene-1,2,4-triol, 2-(diethoxymethyl)benzene-1,3,5-triol, 5-(diethoxymethyl)benzene-1,2,4-triol, 3-(diethoxymethyl)benzene-1,2,4-triol, 1-(diethoxymethyl)-2-methoxybenzene, 1-(diethoxymethyl)-3-methoxybenzene, 1-(diethoxymethyl)-4-methoxybenzene, 1-(diethoxymethyl)-2-ethoxybenzene, 1-(diethoxymethyl)-3-ethoxybenzene, 1-(diethoxymethyl)-4-ethoxybenzene, 1-(diethoxymethyl)-2,3-dimethoxybenzene, 1-(diethoxymethyl)-2,4-dimethoxybenzene, 2-(diethoxymethyl)-1,4-dimethoxybenzene, 2-(diethoxymethyl)-1,3-dimethoxybenzene, 4-(diethoxymethyl)-1,2-dimethoxybenzene, 1-(diethoxymethyl)-3,5-dimethoxybenzene, 1-(diethoxymethyl)-2,3,4-trimethoxybenzene, 1-(diethoxymethyl)-2,3,5-trimethoxybenzene, 2-(diethoxymethyl)-1,3,4-trimethoxybenzene, 2-(diethoxymethyl)-1,3,5-trimethoxybenzene, 1-(diethoxymethyl)-2,4,5-trimethoxybenzene, 2-(diethoxymethyl)-1,3,4-trimethoxybenzene, 4-(diethoxymethyl)-3-methoxyphenol, 4-(diethoxymethyl)-2-methoxyphenol, 5-(diethoxymethyl)-2-methoxyphenol, 2-(diethoxymethyl)-5-methoxyphenol, 4-(diethoxymethyl)-3-ethoxyphenol, 4-(diethoxymethyl)-2-ethoxyphenol, 2-(diethoxymethyl)-5-ethoxyphenol, 5-(diethoxymethyl)-2-ethoxyphenol, 4-(diethoxymethyl)-2,3-dimethoxyphenol, 4-(diethoxymethyl)-2,5-dimethoxyphenol, 4-(diethoxymethyl)-3,5-dimethoxyphenol, 4-(diethoxymethyl)-2,6-dimethoxyphenol, 4-(diethoxymethyl)-2,6-diethoxyphenol, 4-(diethoxymethyl)-3,5-diethoxyphenol, 4-(diethoxymethyl)-3-methylphenol, 4-(diethoxymethyl)-2-methylphenol, 4-(diethoxymethyl)-2,3-dimethylphenol, 4-(diethoxymethyl)-2,5-dimethylphenol, 4-(diethoxymethyl)-3,5-dimethylphenol, 4-(diethoxymethyl)-2,6-dimethylphenol, N-[4-(diethoxymethyl)phenyl]-N,N-dibutylamine, N-[3-chloro-4-(diethoxymethyl)phenyl]-N,N-dimethylamine, N-[4-(diethoxymethyl)-3-methylphenyl]-N,N-dimethylamine, N-[4-(diethoxymethyl)-3-methoxyphenyl]-N,N- dimethylamine, N-[2-(diethoxymethyl)phenyl]-N,N-dimethylamine, N-[4-(diethoxymethyl)phenyl]-N,N-dimethylamine, N-[4-(diethoxymethyl)phenyl]-N,N-diethylamine, 2-(diethoxymethyl)-5-(dimethylamino)phenol, 2-(diethoxymethyl)-5-(diethylamino)phenol, 1-[4-(diethoxymethyl)phenyl]pyrrolidine, 1-[4-(diethoxymethyl)phenyl]piperidine, 4-[4-(diethoxymethyl)phenyl]morpholine, 4-[2-(diethoxymethyl)phenyl]morpholine, 1-(diethoxymethyl)-2-methoxynaphthalene, 1-(diethoxymethyl)-4-methoxynaphthalene, 1-(diethoxymethyl)-2-naphthol, 4-(diethoxymethyl)-1-naphthol, 4-(diethoxymethyl)naphthalene-1,3-diol, 4-(diethoxymethyl)-2-methoxy-1-naphthol, 1-(diethoxymethyl)-4-methoxy-2-naphthol, 4-(diethoxymethyl)-1-methoxy-2-naphthol, 1-(diethoxymethyl)-2,4-dimethoxynaphthalene, 4-(diethoxymethyl)-1,2-dimethoxynaphthalene, N-[4-(diethoxymethyl)-1-naphthyl]-N,N-dimethylamine, N-{4-[3,3-diethoxyprop-1-enyl]phenyl}-N,N-dimethylamine, N-{4-[3,3-diethoxyprop-1-enyl]phenyl}-N,N-diethylamine and 4-(3,3-diethoxyprop-1-enyl)-2-methoxyphenol.

In the agents according to the invention, very particular preference is given to using benzaldehyde, cinnamaldehyde and naphthaldehyde, and derivatives thereof, in particular, with one or more hydroxy, alkoxy or amino substituents, as component B. Here in turn, preference is given to the compounds according to formula V

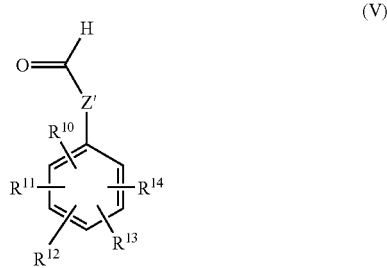

(V)

in which
R$^{10}$, R$^{11}$ and R$^{12}$, independently of one another, are a hydrogen atom, a halogen atom, a C$_1$–C$_6$-alkyl group, a hydroxy group, a C$_1$–C$_6$-alkoxy group, an amino group, a C$_1$–C$_6$-dialkylamino group, a di(C$_2$–C$_6$-alkoxyalkyl)amino group, a di(C$_1$–C$_6$-alkoxy-C$_1$–C$_6$-alkyl)amino group, a C$_1$–C$_6$-hydroxyalkyloxy group, a sulfonyl group, a carboxyl group, a sulfonic acid group, a sulfonamido group, a sulfonamide group, a carbamoyl group, a C$_2$–C$_6$-acyl group, an acetyl group or a nitro group,
Z' is a direct bond or a vinylene group,
R$^{13}$ and R$^{14}$ are a hydrogen atom or jointly form, together with the remainder of the molecule, a 5- or 6-membered aromatic or aliphatic ring.

Very particularly preferred compounds of component B are selected from the group consisting of vanillin, coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methoxybenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,4-dihydroxy-5-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaidehyde, 2,5,6-trihydroxybenzaldehyde, 3,4,5-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde and piperonal.

In a second embodiment, it may be advantageous, to extend the color spectrum and also to improve the fastness properties, to add to the agents according to the invention, besides at least one compound according to formula I and at least one reactive carbonyl compound (component B), at least one further compound as component C, selected from (a) CH-acidic compounds and (b) compounds with a primary or secondary amino or hydroxy group, selected from aromatic hydroxy compounds, primary or secondary aromatic amines and nitrogen-containing heterocyclic compounds.

The CH-acidic compounds of component C are preferably selected from the group consisting of 1,2,3,3-tetramethyl-3H-indolium iodide, 1,2,3,3-tetramethyl-3H-indolium p-toluenesulfonate, 1,2,3,3-tetramethyl-3H-indolium methanesulfonate, 1,3,3-trimethyl-2-methyleneindoline (Fischer's base), 2,3-dimethylbenzothiazolium iodide, 2,3-dimethylbenzothiazolium p-toluenesulfonate, 2,3-dimethyinaphtho[1,2-d]thiazolium p-toluenesulfonate, 3-ethyl-2-methyinaphtho[1,2-d]thiazolium p-toluenesulfonate, rhodanine, rhodanine-3-acetic acid, 1,4-dimethylquinolinium iodide, 1,2-dimethylquinolinium iodide, barbituric acid, thiobarbituric acid, 1,3-dimethylthiobarbituric acid, 1,3-diethylthiobarbituric acid, 1,3-diethylbarbituric acid, oxindole, 3-indoxyl acetate, 2-coumaranone, 5-hydroxy-2-coumaranone, 6-hydroxy-2-coumaranone, 3-methyl-1-phenylpyrazolin-5-one, indane-1,2-dione, indane-1,3-dione, indan-1-one, benzoylacetonitrile, 3-dicyanomethyleneindan-1-one, 2-amino-4-imino-1,3-thiazoline hydrochloride, 5,5-dimethylcyclohexane-1,3-dione, 2H-1,4-benzoxazin-4H-3-one, 3-ethyl-2-methylbenzoxazolium iodide, 3-ethyl-2-methylbenzothiazolium iodide, 1-ethyl-4-methylquinolinium iodide, 1-ethyl-2-methylquinolinium iodide, 1,2,3-trimethylquinoxalinium iodide, 3-ethyl-2-methylbenzoxazolium p-toluenesulfonate, 3-ethyl-2-methylbenzothiazolium p-toluenesulfonate, 1-ethyl-4-methylquinolinium p-toluenesulfonate, 1-ethyl-2-methyl-quinolinium p-toluenesulfonate, 1,2,3-trimethylquinoxalinium p-toluenesulfonate, 1,2-dihydro-1,3,4,6-tetramethyl-2-oxopyrimidinium chloride, 1,2-dihydro-1,3,4,6-tetramethyl-2-oxopyrimidinium hydrogensulfate, 1,2-dihydro-1,3,4-trimethyl-2-oxopyrimidinium chloride, 1,2-dihydro-4,6-dimethyl-1,3-dipropyl-2-oxopyrimidinium chloride, 1,2-dihydro-1,3,4,6-tetramethyl-2-thioxopyrimidinium hydrogensulfate and 2-dihydro-1,3,4,5,6-pentamethyl-2-oxopyrimidinium chloride.

The primary and secondary aromatic amines of component C are preferably selected from the group consisting of N,N-dimethyl-p-phenylenediamine, N,N-diethyl-p-phenylenediamine, N-(2-hydroxyethyl)-N-ethyl-p-phenylenediamine, N,N-bis(2-hydroxyethyl)-p-phenylenediamine, N-(2-methoxyethyl)-p-phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, 2,5-diaminotoluene, 2,5-diaminophenol, 2,5-diaminoanisole, 2,5-diaminophenethol, 4-amino-3-methylphenol, 2-(2,5-diaminophenyl)ethanol, 2,4-diaminophenoxyethanol, 2-(2,5-diaminophenoxy)ethanol, 3-amino-4-(2-hydroxyethyloxy)phenol, 3,4-methylened ioxyphenol, 3,4-methylened ioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 3-amino-2-chloro-6-methylphenol, 2-methyl-5-amino-4-chlorophenol, 5-(2-hydroxyethylamino)-4-methoxy-2-methylphenol, 4-amino-2-hydroxymethylphenol, 2-(diethylaminomethyl)-4-aminophenol, 4-amino-1-hydroxy-2-(2-hydroxyethylaminomethyl)benzene, 1-hydroxy-2-amino-5-methylbenzene, 1-hydroxy-2-amino-6-methylbenzene, 2-amino-5-acetamidophenol, 1,3-dimethyl-2,5-diaminobenzene, 5-(3-hydroxypropylamino)-2-methylphenol, 5-amino-4-methoxy-2-methylphenol, N,N-dimethyl-3-aminophenol, N-cyclopentyl-3-aminophenol, 5-amino-4-fluoro-2-methylphenol, 2,4-diamino-5-fluorotoluene, 2,4-diamino-5-(2-hydroxyethoxy)toluene, 2,4-diamino-5-methylphenetol, 3,5-diamino-2-methoxy-1-methylbenzene, 2-amino-4-(2-hydroxyethylamino)anisole, 2,6-bis(2-hydroxyethylamino)-1-methylbenzene, 1,3-diamino-2,4-dimethoxybenzene, 3,5-diamino-2-methoxytoluene, 2-aminobenzoic acid, 3-aminobenzoic acid, 4-aminobenzoic acid, 2-aminophenylacetic acid, 3-aminophenylacetic acid, 4-aminophenylacetic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-aminobenzenesulfonic acid, 3-aminobenzenesulfonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechin, 4,6-diaminopyrogallol, 1-(2-hydroxy-5-aminobenzyl)-2-imidazolidinone, 4-amino-2-((4-[(5-amino-2-hydroxyphenyl)methyl]piperazinyl)methyl) phenol, 3,5-diamino-4-hydroxypyrocatechin, 1,4-bis(4-aminophenyl)-1,4-diazacycloheptane, aromatic nitriles, such as 2-amino-4-hydroxybenzonitrile, 4-amino-2-hydroxybenzonitrile, 4-aminobenzonitrile, 2,4-diaminobenzonitrile, amino compounds containing nitro groups, such as 3-amino-6-methylamino-2-nitropyridine, picramic acid, [8-[(4-amino-2-nitrophenyl)azo]-7-hydroxynaphth-2-yl]trimethylammonium chloride, [8-((4-amino-3-nitrophenyl)azo)-7-hydroxynaphth-2-yl]trimethylammonium chloride (Basic Brown 17), 1-hydroxy-2-amino-4,6-dinitrobenzene, 1-amino-2-nitro-4-[bis(2-hydroxyethyl)amino]benzene, 1-amino-2-[(2-hydroxyethyl)amino]-5-nitrobenzene (HC Yellow No. 5), 1-amino-2-nitro-4-[(2-hydroxyethyl)amino] benzene (HC Red No. 7), 2-chloro-5-nitro-N-2-hydroxyethyl-1,4-phenylenediamine, 1-[(2-hydroxyethyl)amino]-2-nitro-4-aminobenzene (HC Red No. 3), 4-amino-3-nitrophenol, 4-amino-2-nitrophenol, 6-nitro-o-toluidine, 1-amino-3-methyl-4-[(2-hydroxyethyl)amino]-6-nitrobenzene (HC Violet No. 1), 1-amino-2-nitro-4-[(2,3-dihydroxypropyl)amino]-5-chlorobenzene (HC Red No. 10), 2-(4-amino-2-nitroanilino)benzoic acid, 6-nitro-2,5-diaminopyridine, 2-amino-6-chloro-4-nitrophenol, 1-amino-2-(3-nitrophenylazo)-7-phenylazo-8-naphthol-3,6-disulfonic acid disodium salt (Acid Blue No. 29), 1-amino-2-(2-hydroxy-4-nitrophenylazo)-8-naphthol-3,6-disulfonic acid disodium salt (palatine chrome green), 1-amino-2-(3-chloro-2-hydroxy-5-nitrophenylazo)-8-naphthol-3,6-disulfonic acid disodium salt (Gallion), 4-amino-4'-nitrostilbene-2,2'-disulfonic acid disodium salt, 2,4-diamino-3',5'-dinitro-2'-hydroxy-5-methylazobenzene (Mordant Brown 4), 4'-amino-4-nitrodiphenylamine-2-sulfonic acid, 4'-amino-3'-nitrobenzophenone-2-carboxylic acid, 1-amino-4-nitro-2-(2-nitrobenzylideneamino)benzene, 2-[2-(diethylamino) ethylamino]-5-nitroaniline, 3-amino-4-hydroxy-5-nitrobenzenesulfonic acid, 3-amino-3'-nitrobiphenyl, 3-amino-4-nitroacenaphthene, 2-amino-1-nitronaphthalene, 5-amino-6-nitrobenzo-1,3-dioxole, anilines, in particular, anilines containing nitro groups, such as 4-nitroaniline, 2-nitroaniline, 1,4-diamino-2-nitrobenzene, 1,2-diamino-4-nitrobenzene, 1-amino-2-methyl-6-nitrobenzene, 4-nitro-1,3-phenylenediamine, 2-nitro-4-amino-1-(2-hydroxyethylamino)benzene, 2-nitro-1-amino-4-[bis(2-hydroxyethyl)amino]benzene, 4-amino-2-nitrodiphenylamine-2'-carboxylic acid, 1-amino-5-chloro-4-(2-hydroxyethylamino)-2-nitrobenzene, aromatic anilines and phenols with a further aromatic radical as shown in formula VI

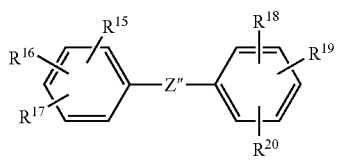

in which
- $R^{15}$ is a hydroxy or an amino group which may be substituted by $C_1$–$C_6$-alkyl, $C_1$–$C_6$-hydroxyalkyl, $C_1$–$C_6$-alkoxy or $C_1$–$C_6$-alkoxy-$C_1$–$C_6$-alkyl groups,
- $R^{16}$, $R^{17}$, $R^{18}$, $R^{19}$ and $R^{20}$, independently of one another, are a hydrogen atom, a hydroxy or an amino group which may be substituted by $C_1$–$C_6$-alkyl, $C_1$–$C_6$-hydroxyalkyl, $C_1$–$C_6$-alkoxy, $C_1$–$C_6$-aminoalkyl or $C_1$–$C_6$-alkoxy-$C_1$–$C_6$-alkyl groups, and
- Z″ is a direct bond, a saturated or unsaturated carbon chain optionally substituted by hydroxy groups and having 1 to 4 carbon atoms, a carbonyl group, sulfonyl group or imino group, an oxygen atom or sulfur atom, or a group with the formula VII

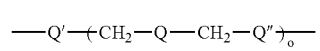

in which
- Q is a direct bond, a $CH_2$ group or CHOH group,
- Q′ and Q″, independently of one another, are an oxygen atom, an $NR^{21}$ group, in which $R^{21}$ is a hydrogen atom, a $C_1$–$C_6$-alkyl group or $C_1$–$C_6$-hydroxyalkyl group, where also the two groups, together with the remaining molecule, can form a 5-, 6- or 7-membered ring, the group O—$(CH_2)_p$—NH or NH—$(CH_2)_{p'}$—O, in which p and p′ are 2 or 3, and
- o is a number from 1 to 4, such as, in particular, 4,4′-diaminostilbene and its hydrochloride, 4,4′-diaminostilbene-2,2′-disulfonic acid mono- or di-Na salt, 4-amino-4′-dimethylaminostilbene and its hydrochloride, 4,4′-diaminodiphenylmethane, 4,4′-diaminodiphenyl sulfide, 4,4′-diaminodiphenyl sulfoxide, 4,4′-diaminodiphenylamine, 4,4′-diaminodiphenylamine-2-sulfonic acid, 4,4′-diaminobenzophenone, 4,4′-diaminodiphenyl ether, 3,3′,4,4′-tetraaminodiphenyl, 3,3′,4,4′-tetraaminobenzophenone, 1,3-bis(2,4-diaminophenoxy)propane, 1,8-bis(2,5-diaminophenoxy)-3,6-dioxaoctane, 1,3-bis(4-aminophenylamino)propane, 1,3-bis(4-aminophenylamino)-2-propanol, 1,3-bis[N-(4-aminophenyl)-2-hydroxyethylamino]-2-propanol, N,N-bis[2-(4-aminophenoxy)ethyl]methylamine, N-phenyl-1,4-phenylenediamine and bis(5-amino-2-hydroxyphenyl)methane.

The nitrogen-containing heterocyclic compounds of component C are preferably selected from the group consisting of 2-aminopyridine, 3-aminopyridine, 4-aminopyridine, 2-amino-3-hydroxypyridine, 2,6-diaminopyridine, 2,5-diaminopyridine, 2-(aminoethylamino)-5-aminopyridine, 2,3-diaminopyridine, 2-dimethylamino-5-aminopyridine, 2-methylamino-3-amino-6-methoxypyridine, 2,3-diamino-6-methoxypyridine, 2,6-dimethoxy-3,5-diaminopyridine, 2,4,5-triaminopyridine, 2,6-dihydroxy-3,4-dimethylpyridine, N-[2-(2,4-diaminophenyl)aminoethyl]-N-(5-amino-2-pyridyl)amine, N-[2-(4-aminophenyl)aminoethyl]-N-(5-amino-2-pyridyl)amine, 2,4-dihydroxy-5,6-diaminopyrimidine, 4,5,6-triaminopyrimidine, 4-hydroxy-2,5,6-triaminopyrimidine, 2-hydroxy-4,5,6-triaminopyrimidine, 2,4,5,6-tetraaminopyrimidine, 2-methylamino-4,5,6-triaminopyrimidine, 2,4-diaminopyrimidine, 4,5-diaminopyrimidine, 2-amino-4-methoxy-6-methylpyrimidine, 3,5-diaminopyrazole, 3,5-diamino-1,2,4-triazole, 3-aminopyrazole, 3-amino-5-hydroxypyrazole, 1-phenyl-4,5-diaminopyrazole, 1-(2-hydroxyethyl)-4,5-diaminopyrazole, 1-phenyl-3-methyl-4,5-diaminopyrazole, 4-amino-2,3-dimethyl-1-phenyl-3-pyrazolin-5-one (4-aminoantipyrin), 1-phenyl-3-methylpyrazol-5-one, 2-aminoquinoline, 3-aminoquinoline, 8-aminoquinoline, 4-aminoquinaldine, 2-aminonicotinic acid, 6-aminonicotinic acid, 5-aminoisoquinoline, 5-aminoindazole, 6-aminoindazole, 5-aminobenzimidazole, 7-aminobenzimidazole, 5-aminobenzothiazole, 7-aminobenzothiazole, 2,5-dihydroxy-4-morpholinoaniline, and indole and indoline derivatives, such as 4-aminoindole, 5-aminoindole, 6-aminoindole, 7-aminoindole, 5,6-dihydroxyindole, and 4-hydroxyindoline. In addition, heterocyclic compounds which can be used according to the invention are the hydoxypyrimidines disclosed in DE-U1-299 08 573. The above-mentioned compounds can be used either in free form or in the form of their physiologically compatible salts, e.g., as salts of inorganic acids, such as hydrochloric acid or sulfuric acid.

The aromatic hydroxy compounds of component C are preferably selected from the group consisting of 2-methylresorcinol, 4-methylresorcinol, 5-methylresorcinol, 2,5-dimethylresorcinol, resorcinol, 3-methoxyphenol, pyrocatechin, hydroquinone, pyrogallol, phloroglucine, hydroxyhydroquinone, 2-methoxyphenol, 3-methoxyphenol, 4-methoxyphenol, 3-dimethylaminophenol, 2-(2-hydroxyethyl)phenol, 3,4-methylenedioxyphenol, 2,4-dihydroxybenzoic acid, 3,4-dihydroxybenzoic acid, 1-(2,4-dihydroxyphenyl)acetic acid, 1-(3,4-dihydroxyphenyl) acetic acid, gallic acid, 2,4,6-trihydroxybenzoic acid, -acetophenone, 2-chlororesorcinol, 4-chlororesorcinol, 1-naphthol, 1,5-dihydroxynaphthalene, 2,3-dihydroxynaphthalene, 2,7-dihydroxynaphthalene, 6-dimethylamino-4-hydroxy-2-naphthalenesulfonic acid and 3,6-dihydroxy-2,7-naphthalenesulfonic acid.

In a third embodiment, the colorant additionally comprises at least one reaction product (referred to below as reaction product RP) from a compound of the formula I and a compound of component B, in particular, compounds according to formula II, as direct dye. Such reaction products RP can be obtained, for example, by heating the two reactants in aqueous neutral to weakly alkaline medium, where the reaction products RP either precipitate out of the solution as solid or are isolated therefrom by evaporating the solution.

In the agents according to the invention, reaction products RP according to formula VIII can thus be present,

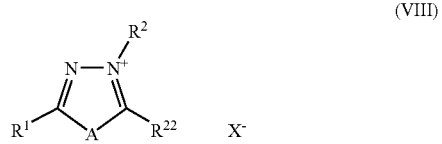

in which
R¹, R², A and X⁻ are defined as described under formula I,
R²² is a group according to formula IX,

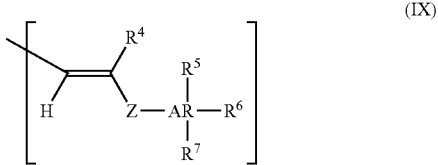

(IX)

in which
R⁴, R⁵, R⁶, R⁷, AR and Z are defined as described under formula II.

For the synthesis of the reaction products RP, molar ratios of component B to the compound according to formula I of from about 1:1 to about 2:1 may be useful.

It is particularly preferred if the agents according to the invention comprise those reaction products RP according to formula VIII in which the radical A is an oxygen atom or sulfur atom.

It is particularly preferred if the agents according to the invention comprise those reaction products RP according to formula VIII in which AR according to formula IX is benzene or naphthalene.

It is also particularly preferred if the agents according to the invention comprise those reaction products RP according to formula VIII in which Z according to formula IX is a direct bond or vinylene.

It is also particularly preferred if the agents according to the invention comprise those reaction products RP according to formula VIII in which R⁴ according to formula IX is a hydrogen atom.

The above-mentioned compounds with the formula I, the compounds of component B, component C and the reaction products RP are in each case preferably used in an amount of from 0.03 to 65 mmol, in particular, from 1 to 40 mmol, based on 100 g of the total colorant.

In a fourth embodiment, the agents according to the invention comprise, besides at least one compound according to formula I and at least one reactive carbonyl compound, at least one developer component and optionally at least one coupler component as oxidation dye precursors.

According to the invention, it may be preferred to use a p-phenylenediamine derivative or one of its physiologically compatible salts as developer component. Particular preference is given to p-phenylenediamine derivatives of the formula (E1)

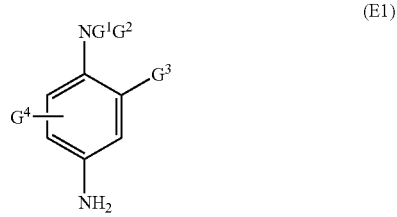

(E1)

where
G¹ is a hydrogen atom, a C₁- to C₄-alkyl radical, a C₁- to C₄-monohydroxyalkyl radical, a C₂- to C₄-polyhydroxyalkyl radical, a (C₁- to C₄)-alkoxy-(C₁- to C₄)-alkyl radical, a 4'-aminophenyl radical or a C₁- to C₄-alkyl radical which is substituted by a nitrogen-containing group, a phenyl radical or a 4'-aminophenyl radical;

G² is a hydrogen atom, a C₁- to C₄-alkyl radical, a C₁- to C₄-monohydroxyalkyl radical, a C₂- to C₄-polyhydroxyalkyl radical, a (C₁- to C₄)-alkoxy-(C₁- to C₄)-alkyl radical or a C₁- to C₄-alkyl radical which is substituted by a nitrogen-containing group;

G³ is a hydrogen atom, a halogen atom, such as a chlorine atom, bromine atom, iodine atom or fluorine atom, a C₁- to C₄-alkyl radical, a C₁- to C₄-monohydroxyalkyl radical, a C₂- to C₄-polyhydroxyalkyl radical, a C₁- to C₄-hydroxyalkoxyradical, a C₁ to C₄-acetylaminoalkoxy radical, a C₁- to C₄-mesylaminoalkoxy radical or a C₁- to C₄-carbamoylaminoalkoxy radical;

G⁴ is a hydrogen atom, a halogen atom or a C₁- to C₄-alkyl radical or if G³ and G⁴ are in the ortho position relative to one another, they can together form a bridging α, ω-alkylenedioxo group, such as, for example, an ethylenedioxy group.

Examples of nitrogen-containing groups of the formula (E1) are, in particular, the amino groups, C₁- to C₄-monoalkylamino groups, C₁- to C₄-dialkylamino groups, C₁- to C₄-trialkylammonium groups, C₁- to C₄-monohydroxyalkylamino groups, imidazolinium and ammonium.

Particularly preferred p-phenylenediamines of the formula (E1) are selected from p-phenylenediamine, p-tolylenediamine, 2-chloro-p-phenylenediamine, 2,3-dimethyl-p-phenylenediamine, 2,6-dimethyl-p-phenylenediamine, 2,6-diethyl-p-phenylenediamine, 2,5-dimethyl-p-phenylenediamine, N,N-dimethyl-p-phenylenediamine, N,N-diethyl-p-phenylenediamine, N,N-dipropyl-p-phenylenediamine, 4-amino-3-methyl-(N,N-diethyl)aniline, N,N-bis(β-hydroxyethyl)-p-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-p-phenylenediamine, 2-(α,β-dihydroxyethyl)-p-phenylenediamine, 2-fluoro-p-phenylenediamine, 2-isopropyl-p-phenylenediamine, N-(β-hydroxypropyl)-p-phenylenediamine, 2-hydroxymethyl-p-phenylenediamine, N,N-dimethyl-3-methyl-p-phenylenediamine, N,N-(ethyl,β-hydroxyethyl)-p-phenylenediamine, N-(β,γ-dihydroxypropyl)-p-phenylenediamine, N-(4'-aminophenyl)-p-phenylenediamine, N-phenyl-p-phenylenediamine, 2-(β-hydroxyethyloxy)-p-phenylenediamine, 2-(β-acetylaminoethyloxy)-p-phenylenediamine, N-(β-methoxyethyl)-p-phenylenediamine and 5,8-diaminobenzo-1,4-dioxane, and their physiologically compatible salts.

According to the invention, very particularly preferred p-phenylenediamine derivatives of the formula (E1) are p-phenylenediamine, p-tolylenediamine, 2-(β-hydroxyethyl)-p-phenylenediamine, 2-(α,β-dihydroxyethyl)-p-phenylenediamine and N,N-bis(β-hydroxyethyl)-p-phenylenediamine.

According to the invention, it may also be preferred to use, as developer component, compounds which contain at least two aromatic nuclei which are substituted by amino and/or hydroxyl groups.

Among the binuclear developer components which can be used in the coloring compositions according to the invention, mention may be made in particular, of the compounds which conform to the following formula (E2), and their physiologically compatible salts:

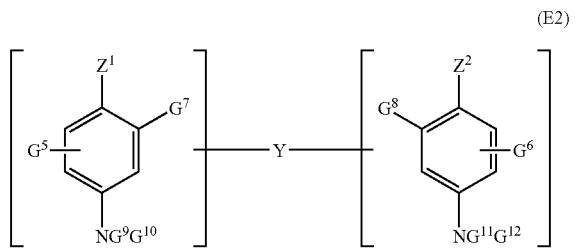

(E2)

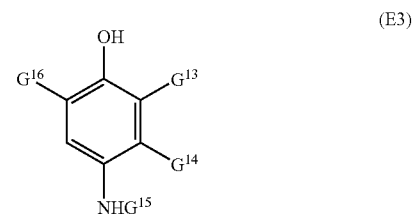

(E3)

where:

$Z^1$ and $Z^2$, independently of one another, are a hydroxyl or $NH_2$ radical which is optionally substituted by a $C_1$- to $C_4$-alkyl radical, by a $C_1$- to $C_4$-hydroxyalkyl radical and/or by a bridge Y or which is optionally part of a bridging ring system, the bridge Y is an alkylene group having 1 to 14 carbon atoms, such as, for example, a linear or branched alkylene chain or an alkylene ring which can be terminated or interrupted by one or more nitrogen-containing groups and/or one or more heteroatoms, such as oxygen, sulfur or nitrogen atoms, and may possibly be substituted by one or more hydroxyl or $C_1$- to $C_8$-alkoxy radicals, or a direct bond, $G^5$ and $G^6$, independently of one another, are a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a $C_1$- to $C_4$-aminoalkyl radical or a direct bond to the bridge Y, $G^7$, $G^8$, $G^9$, $G^{10}$, $G^{11}$ and $G^{12}$, independently of one another, are a hydrogen atom, a direct bond to the bridge Y or a $C_1$- to $C_4$-alkyl radical, with the provisos that the compounds of the formula (E2) contain only one bridge Y per molecule and the compounds of the formula (E2) contain at least one amino group which carries at least one hydrogen atom.

According to the invention, the substituents used in formula (E2) are defined analogously to the above statements.

Preferred binuclear developer components of the formula (E2) are in particular: N,N'-bis(β-hydroxyethyl)-N,N'-bis(4'-aminophenyl)-1,3-diaminopropan-2-ol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-diethyl-N,N'-bis(4'-amino-3'-methylphenyl)ethylenediamine, bis(2-hydroxy-5-aminophenyl)methane, N,N'-bis(4'-aminophenyl)-1,4-diazacycloheptane, N,N'-bis(2-hydroxy-5-aminobenzyl)piperazine, N-(4'-aminophenyl)-p-phenylenediamine and 1,10-bis(2',5'-diaminophenyl)-1,4,7,10-tetraoxadecane and their physiologically compatible salts.

Very particularly preferred binuclear developer components of the formula (E2) are N,N'-bis(β-hydroxyethyl)-N,N'-bis(4'-aminophenyl)-1,3-diaminopropan-2-ol, bis(2-hydroxy-5-aminophenyl)methane, N,N'-bis(4'-aminophenyl)-1,4-diazacycloheptane and 1,10-bis(2',5'-diaminophenyl)-1,4,7,10-tetraoxadecane or one of their physiologically compatible salts.

In addition, it may be preferred according to the invention to use a p-aminophenol derivative or one of its physiologically compatible salts as developer component. Particular preference is given to p-aminophenol derivatives of the formula (E3)

where:

$G^{13}$ is a hydrogen atom, a halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a $C_1$- to $C_4$-aminoalkyl radical, a hydroxy-($C_1$- to $C_4$)-alkylamino radical, a $C_1$- to $C_4$-hydroxyalkoxy radical, a $C_1$- to $C_4$-hydroxyalkyl-($C_1$- to $C_4$)-aminoalkyl radical or a (di-$C_1$- to $C_4$-alkylamino)-($C_1$- to $C_4$)-alkyl radical, and $G^{14}$ is a hydrogen or halogen atom, a $C_1$- to $C_4$-alkyl radical, a $C_1$- to $C_4$-monohydroxyalkyl radical, a $C_2$- to $C_4$-polyhydroxyalkyl radical, a ($C_1$- to $C_4$)-alkoxy-($C_1$- to $C_4$)-alkyl radical, a $C_1$- to $C_4$-aminoalkyl radical or a $C_1$- to $C_4$-cyanoalkyl radical, $G^{15}$ is hydrogen, a $C_1$- to $C_4$-alkyl radical, a $C_1$- to $C_4$-monohydroxyalkyl radical, a $C_2$- to $C_4$-polyhydroxyalkyl radical, a phenyl radical or a benzyl radical, and $G^{16}$ is hydrogen or a halogen atom.

According to the invention, the substituents used in formula (E3) are defined analogously to the above statements.

Preferred p-aminophenols of the formula (E3) are, in particular, p-aminophenol, N-methyl-p-aminophenol, 4-amino-3-methylphenol, 4-amino-3-fluorophenol, 2-hydroxymethylamino-4-aminophenol, 4-amino-3-hydroxymethylphenol, 4-amino-2-(-hydroxyethoxy)phenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-(α,β-dihydroxyethyl)phenol, 4-amino-2-fluorophenol, 4-amino-2-chlorophenol, 4-amino-2,6-dichlorophenol, 4-amino-2-(diethylaminomethyl)phenol and their physiologically compatible salts.

Very particularly preferred compounds of the formula (E3) are p-aminophenol, 4-amino-3-methylphenol, 4-amino-2-aminomethylphenol, 4-amino-2-(α,β-dihydroxyethyl)phenol and 4-amino-2-(diethylaminomethyl)phenol.

In addition, the developer component can be selected from o-aminophenol and its derivatives, such as, for example, 2-amino-4-methylphenol, 2-amino-5-methylphenol or 2-amino-4-chlorophenol.

In addition, the developer component can be selected from heterocyclic developer components, such as, for example, the pyridine, pyrimidine, pyrazole, pyrazolopyrimidine derivatives and their physiologically compatible salts.

Preferred pyridine derivatives are, in particular, the compounds which are described in the patents GB 1 026 978 and GB 1 153 196, such as 2,5-diaminopyridine, 2-(4'-methoxyphenyl)amino-3-aminopyridine, 2,3-diamino-6-methoxypyridine, 2-(β-methoxyethyl)amino-3-amino-6-methoxypyridine and 3,4-diaminopyridine.

Preferred pyrimidine derivatives are, in particular, the compounds which are described in the German patent DE 2 359 399, the Japanese laid-open specification JP 02019576 A2 or in the laid-open specification WO 96/15765, such as 2,4,5,6-tetraaminopyrimidine, 4-hydroxy-2,5,6-triaminopyrimidine, 2-hydroxy-4,5,6-triaminopyrimidine, 2-dimethylamino-4,5,6-triaminopyrimidine, 2,4-dihydroxy-5,6-diaminopyrimidine and 2,5,6-triaminopyrimidine.

Preferred pyrazole derivatives are, in particular, the compounds which are described in the patents DE 3 843 892, DE 4 133 957 and patent applications WO 94/08969, WO 94/08970, EP-740 931 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole.

Preferred pyrazolopyrimidine derivatives are, in particular, the derivatives of pyrazolo[1,5-a]pyrimidine of the following formula (E4) and its tautomeric forms if a tautomeric equilibrium exists:

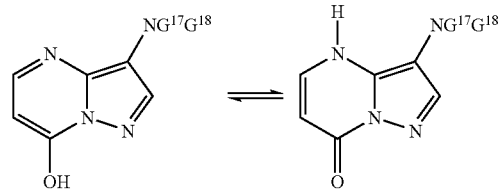

where:
- $G^{17}$, $G^{18}$, $G^{19}$ and $G^{20}$, independently of each other, are a hydrogen atom, a $C_1$–$C_4$-alkyl radical, an aryl radical, a $C_1$–$C_4$-hydroxyalkyl radical, a $C_2$–$C_4$-polyhydroxyalkyl radical, a $(C_1$–$C_4)$-alkoxy-$(C_1$–$C_4)$-alkyl radical, a $C_1$–$C_4$-aminoalkyl radical, which may be optionally protected by an acetyl ureido or a sulfonyl radical, a $(C_1$–$C_4)$-alkylamino-$(C_1$–$C_4)$-alkyl radical, a di[$(C_1$–$C_4)$-alkyl]-$(C_1$–$C_4)$-aminoalkyl radical, where the dialkyl radicals optionally form a carbon cycle or a heterocycle with 5 or 6 chain members, a $C_1$–$C_4$-hydroxyalkyl radical or a di$(C_1$–$C_4)$-[hydroxyalkyl]-$(C_1$–$C_4)$-aminoalkyl radical,
- the X radicals, independently of each other, are a hydrogen atom, a $C_1$–$C_4$-alkyl radical, an aryl radical, a $C_1$–$C_4$-hydroxyalkyl radical, a $C_2$–$C_4$-polyhydroxyalkyl radical, a $C_1$–$C_4$-aminoalkyl radical, a $(C_1$–$C_4)$-alkylamino-$(C_1$–$C_4)$-alkyl radical, a di[$(C_1$–$C_4)$-alkyl]-$(C_1$–$C_4)$-aminoalkyl radical, where the dialkyl radicals optionally form a carbon cycle or a heterocycle with 5 or 6 chain members, a $C_1$–$C_4$-hydroxyalkyl or a di$(C_1$–$C_4$-hydroxyalkyl)aminoalkyl radical, an amino radical, a $C_1$–$C_4$-alkyl- or di$(C_1$–$C_4$-hydroxyalkyl) amino radical, a halogen atom, a carboxylic acid group or a sulfonic acid group,
- i has the value 0, 1, 2 or 3,
- p has the value 0 or 1,
- q has the value 0 or 1 and
- n has the value 0 or 1,
- with the proviso that
- the sum of p+q is not 0,
- if p+q is 2, n has the value 0, and the groups $NG^{17}G^{18}$ and $NG^{19}G^{20}$ occupy the positions (2,3); (5,6); (6,7); (3,5) or (3,7);
- if p+q is 1, n has the value 1, and the groups $NG^{17}G^{18}$ (or $NG^{19}G^{20}$) and the group OH occupy the positions (2,3); (5,6); (6,7); (3,5) or (3,7);

According to the invention, the substituents used in formula (E4) are defined analogously to the above statements.

If the pyrazolo[1,5-a]pyrimidine of the above formula (E4) contains a hydroxy group at one of positions 2, 5 or 7 of the ring system, a tautomeric equilibrium exists which is represented, for example, in the following scheme:

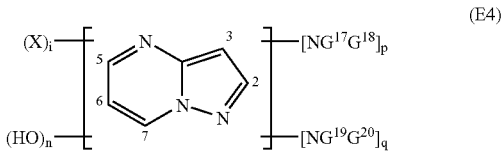

Among the pyrazolo[1,5-a]pyrimidines of the above formula (E4) mention may be made in particular, of:
- pyrazolo[1,5-a]pyrimidine-3,7-diamine;
- 2,5-dimethylpyrazolo[1,5-a]pyrimidine-3,7-diamine;
- pyrazolo[1,5-a]pyrimidine-3,5-diamine;
- 2,7-dimethylpyrazolo[1,5-a]pyrimidine-3,5-diamine;
- 3-aminopyrazolo[1,5-a]pyrimidin-7-ol;
- 3-aminopyrazolo[1,5-a]pyrimidin-5-ol;
- 2-(3-aminopyrazolo[1,5-a]pyrimidin-7-ylamino)ethanol;
- 2-(7-aminopyrazolo[1,5-a]pyrimidin-3-ylamino)ethanol;
- 2-[(3-aminopyrazolo[1,5-a]pyrimidin-7-yl)-(2-hydroxyethyl)amino]ethanol;
- 2-[(7-aminopyrazolo[1,5-a]pyrimidin-3-yl)-(2-hydroxyethyl)amino]ethanol;
- 5,6-dimethylpyrazolo[1,5-a]pyrimidine-3,7-diamine;
- 2,6-dimethylpyrazolo[1,5-a]pyrimidine-3,7-diamine;
- 3-amino-7-dimethylamino-2,5-dimethylpyrazolo[1,5-a] pyrimidine;

and their physiologically compatible salts and their tautomeric forms if a tautomeric equilibrium is present.

The pyrazolo[1,5-a]pyrimidines of the above formula (E4) can be prepared as described in the literature by cyclization starting from an aminopyrazole or from hydrazine.

The coupler components optionally present in the agents according to the invention are preferably selected from
- m-aminophenol and its derivatives, such as, for example, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2'-hydroxyethyl)amino-2-methylphenol, 3-(diethylamino)phenol, N-cyclopentyl-3- aminophenol, 1,3-dihydroxy-5-(methylamino)benzene, 3-ethylamino-4-methylphenol and 2,4-dichloro-3-aminophenol, o-aminophenol and derivatives thereof, m-diaminobenzene and derivatives thereof, such as, for example, 2,4-diaminophenoxyethanol, 1,3-bis(2',4'-diaminophenoxy)propane, 1-methoxy-2-amino-4-(2'-hydroxyethylamino)benzene, 1,3-bis(2',4'-diaminophenyl)propane, 2,6-bis(2'-hydroxyethylamino)-1-methylbenzene and 1-amino-3-bis(2'-hydroxyethyl)aminobenzene, o-diaminobenzene and derivatives thereof, such as, for example, 3,4-diaminobenzoic acid and 2,3-diamino-1-methylbenzene, di- and trihydroxybenzene derivatives, such as, for example, resorcinol, resorcinol monomethyl ether, 2-methylresorcinol, 5-methylresorcinol, 2,5-dimethylresorcinol, 2-chlororesorcinol, 4-chlororesorcinol, pyrogallol and 1,2,4-trihydroxybenzene, pyridine derivatives, such as, for example, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethyl pyridine, 2,6-dihydroxy-4-methylpyridine, 2,6-diaminopyridine, 2,3-diamino-6-methoxypyridine and 3,5-diamino-2,6-dimethoxypyridine, naphthalene derivatives, such as, for example, 1-naphthol, 2-methyl-1-naphthol, 2-hydroxymethyl-1-naphthol, 2-hydroxyethyl-1-naphthol, 1,5-dihydroxynaphthalene, 1,6-dihydroxynaphthalene, 1,7-dihydroxynaphthalene, 1,8-dihydroxynaphthalene, 2,7-dihydroxynaphthalene and 2,3-dihydroxynaphthalene, morpholine derivatives, such as, for example, 6-hydroxybenzomorpholine and 6-aminobenzomorpholine, quinoxaline derivatives, such as, for example, 6-methyl-1,2,3,4-tetrahydroquinoxaline, pyrazole derivatives, such as, for example, 1-phenyl-3-methylpyrazol-5-one, indole derivatives, such as, for example, 4-hydroxyindole, 6-hydroxyindole and 7-hydroxyindole, pyrimidine derivatives, such as, for example, 4,6-diaminopyrimidine, 4-amino-2,6-dihydroxypyrimidine, 2,4-diamino-6-hydroxypyrimidine, 2,4,6-trihydroxypyrimidine, 2-amino-4-methylpyrimidine, 2-amino-4-hydroxy-6-methylpyrimidine, and 4,6-dihydroxy-2-methylpyrimidine, or methylenedioxybenzene derivatives, such as, for example, 1-hydroxy-3,4-methylenedioxybenzene, 1-amino-3,4-methylenedioxybenzene and 1-(2-hydroxyethyl)amino-3,4-methylenedioxybenzene.

Coupler components which are particularly preferred according to the invention are 1-naphthol, 1,5-, 2,7- and 1,7-dihydroxynaphthalene, 3-aminophenol, 5-amino-2-methylphenol, 2-amino-3-hydroxypyridine, resorcinol, 4-chlororesorcinol, 2-chloro-6-methyl-3-aminophenol, 2-methylresorcinol, 5-methylresorcinol, 2,5-dimethylresorcinol and 2,6-dihydroxy-3,4-dimethylpyridine.

Within the scope of a fifth embodiment, precursors of nature-analogous dyes which may be used in the agents according to the invention are also preferably those indoles and indolines which have at least one hydroxy or amino group, preferably as substituent on the six-membered ring. These groups can carry further substituents, e.g., in the form of an etherification or esterification of the hydroxy group or an alkylation of the amino group. In a second preferred embodiment, the colorants comprise at least one indole derivative and/or indoline derivative.

Particularly suitable precursors of nature-analogous hair dyes are derivatives of 5,6-dihydroxyindoline of the formula Xa,

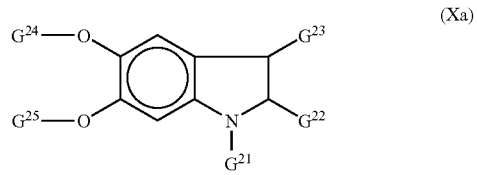

(Xa)

in which, independently of one another, $G^{21}$ is hydrogen, a $C_1$–$C_4$-alkyl group or a $C_1$–$C_4$-hydroxyalkyl group, $G^{22}$ is hydrogen or a —COOH group, where the —COOH group can also be in the form of a salt with a physiologically compatible cation, $G^{23}$ is hydrogen or a $C_1$–$C_4$-alkyl group, $G^{24}$ is hydrogen, a $C_1$–$C_4$-alkyl group or a group —CO-$G^{26}$, in which $G^{26}$ is a $C_1$–$C_4$-alkyl group, and $G^{25}$ is one of the groups specified under $G^{24}$, and physiologically compatible salts of these compounds with an organic or inorganic acid.

Particularly preferred derivatives of indoline are 5,6-dihydroxyinodoline, N-methyl-5,6-dihydroxyindoline, N-ethyl-5,6-dihydroxyindoline, N-propyl-5,6-dihydroxyindoline, N-butyl-5,6-dihydroxyindoline, 5,6-dihydroxyindoline-2-carboxylic acid, and 6-hydroxyindoline, 6-aminoindoline and 4-aminoindoline.

Within this group, particular emphasis is given to N-methyl-5,6-dihydroxyindoline, N-ethyl-5,6-dihydroxyindoline, N-propyl-5,6-dihydroxyindoline, N-butyl-5,6-dihydroxyindoline and, in particular, 5,6-dihydroxyindoline.

Exceptionally suitable precursors of nature-analogous hair dyes are also derivatives of 5,6-dihydroxyindole of the formula Xb,

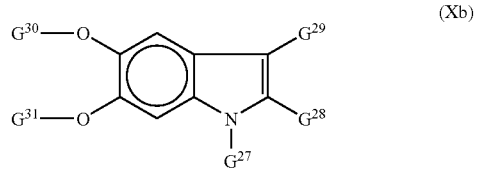

(Xb)

in which, independently of one another, $G^{27}$ is hydrogen, a $C_1$–$C_4$-alkyl group or a $C_1$–$C_4$-hydroxyalkyl group, $G^{28}$ is hydrogen or a —COOH group, where the —COOH group may also be in the form of a salt with a physiologically compatible cation, $G^{29}$ is hydrogen or a $C_1$–$C_4$-alkyl group, $G^{30}$ is hydrogen, a $C_1$–$C_4$-alkyl group or a group —CO-$G^{32}$, in which $G^{32}$ is a $C_1$–$C_4$-alkyl group, and $G^{31}$ is one of the groups specified under $G^{30}$, and physiologically compatible salts of these compounds with an organic or inorganic acid.

Particularly preferred derivatives of indole are 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, 6-hydroxyindole, 6-aminoindole and 4-aminoindole.

Within this group, emphasis is placed on N-methyl-5,6-dihydroxyindole, N-ethyl-5,6-dihydroxyindole, N-propyl-5,6-dihydroxyindole, N-butyl-5,6-dihydroxyindole and, in particular, 5,6-dihydroxyindole.

The indoline and indole derivatives can be used in the colorants according to the invention either as free bases or in the form of their physiologically compatible salts with inorganic or organic acids, e.g., the hydrochlorides, sulfates and hydrobromides. The indole derivatives and indoline derivatives are present in these usually in amounts of 0.05–10% by weight, preferably 0.2–5% by weight.

In a sixth embodiment, besides the compounds present according to the invention, the colorants according to the invention additionally comprise, for modifying the color nuances, customary direct dyes, such as nitrophenylenediamines, nitroaminophenols, azo dyes, anthaquinones or indophenols. Preferred direct dyes are the compounds known under the international names or trade names HC Yellow 2, HC Yellow 4, HC Yellow 5, HC Yellow 6, HC Yellow 12, Acid Yellow 1, Acid Yellow 10, Acid Yellow 23, Acid Yellow 36, HC Orange 1, Disperse Orange 3, Acid Orange 7, HC Red 1, HC Red 3, HC Red 10, HC Red 11, HC Red 13, Acid Red 33, Acid Red 52, HC Red BN, Pigment Red 57:1, HC Blue 2, HC Blue 12, Disperse Blue 3, Acid Blue 7, Acid Green 50, HC Violet 1, Disperse Violet 1, Disperse Violet 4, Acid Violet 43, Disperse Black 9, Acid Black 1, and Acid Black 52, and 1,4-diamino-2-nitrobenzene, 2-amino-4-nitrophenol, 1,4-bis(β-hydroxethyl)amino-2-nitrobenzene, 3-nitro-4-(β-hydroxyethyl)aminophenol, 2-(2'-hydroxyethyl)amino-4,6-dinitrophenol, 1-(2'-hydroxyethyl)amino-4-methyl-2-nitrobenzene, 1-amino-4-(2'-hydroxyethyl)amino-5-chloro-2-nitrobenzene, 4-amino-3-nitrophenol, 1-(2'-ureidoethyl)amino-4-nitrobenzene, 4-amino-2-nitrodiphenylamine-2'-carboxylic acid, 6-nitro-1,2,3,4-tetrahydroquinoxaline, 2-hydroxy-1,4-naphthoquinone, picraminic acid and salts thereof, 2-amino-6-chloro-4-nitrophenol, 4-ethylamino-3-nitrobenzoic acid and 2-chloro-6-ethylamino-1-hydroxy-4-nitrobenzene.

In addition, the agents according to the invention can preferably comprise a cationic direct dye. Particular preference is given here to (a) cationic triphenylmethane dyes, such as, for example, Basic Blue 7, Basic Blue 26, Basic Violet 2 and Basic Violet 14, (b) aromatic systems which are substituted by a quaternary nitrogen group, such as, for example, Basic Yellow 57, Basic Red 76, Basic Blue 99, Basic Brown 16 and Basic Brown 17, and (c) direct dyes which contain a heterocycle which has at least one quaternary nitrogen atom, as are specified, for example, in EP-A2-998 908, to which reference is explicitly made at this point, in claims 6 to 11.

Preferred cationic direct dyes of group (c) are, in particular, the following compounds:

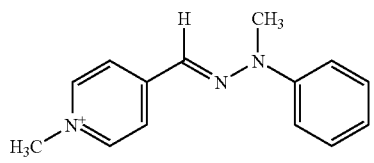
(DZ1)
(Basic Yellow 87)

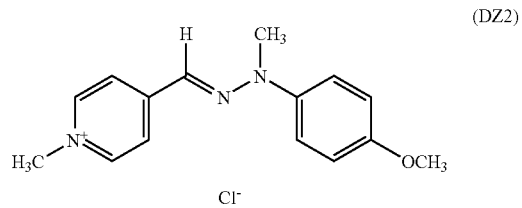
(DZ2)

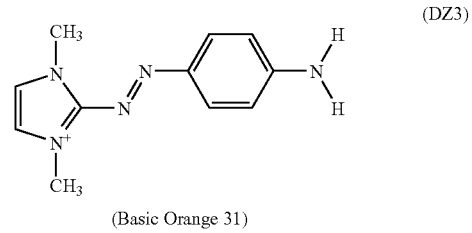
(DZ3)
(Basic Orange 31)

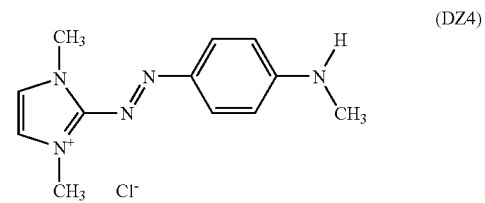
(DZ4)

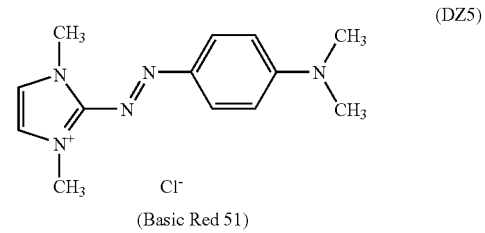
(DZ5)
(Basic Red 51)

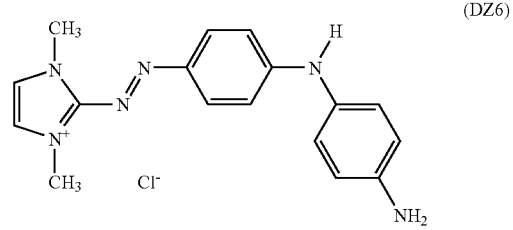
(DZ6)

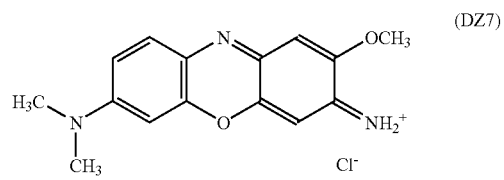
(DZ7)

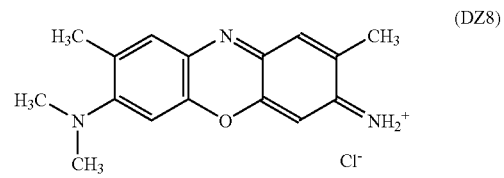
(DZ8)

-continued

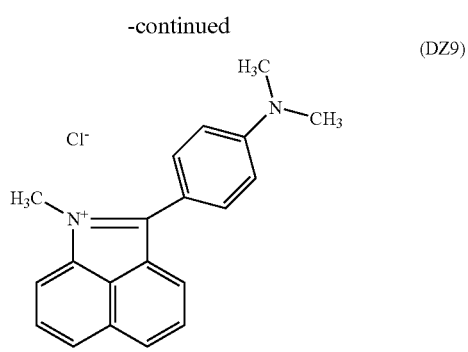

(DZ9)

The compounds of the formulae (DZ1), (DZ3) and (DZ5) are very particularly preferred cationic direct dyes of group (c). The cationic direct dyes which are sold under the trade name Arianor® are particularly preferred direct dyes according to the invention.

The agents according to the invention in accordance with this embodiment comprise the direct dyes preferably in an amount of from 0.01 to 20% by weight, based on the total colorant.

In addition, the preparations according to the invention can also comprise naturally occurring dyes, such as, for example, henna red, henna neutral, henna black, camomile blossom, sandalwood, black tea, buckthorn bark, sage, logwood, madder root, catechu, sedre and alkanna root.

It is not necessary for the optionally present direct dyes to each constitute uniform compounds. Instead, as a result of the preparation processes for the individual dyes, it is also possible for further components to be present in the colorants according to the invention provided these do not adversely affect the coloring result or have to be excluded for other reasons, e.g., toxicological reasons.

To achieve further and more intense colorations, the agents according to the invention can additionally comprise color enhancers. The color enhancers are preferably selected from the group consisting of piperidine, piperidine-2-carboxylic acid, piperidine-3-carboxylic acid, piperidine-4-carboxylic acid, piperidine, 2-hydroxypyridine, 3-hydroxypyridine, 4-hydroxypyridine, imidazole, 1-methylimidazole, arginine, histidine, pyrrolidine, proline, pyrrolidone, pyrrolidione-5-carboxylic acid, pyrazole, 1,2,4-triazole, piperazidine, derivatives thereof, and physiologically compatible salts thereof.

The above-mentioned color enhancers may be used in an amount of in each case 0.03 to 65 mmol, in particular, 1 to 40 mmol, in each case based on 100 g of the total colorant.

The presence of oxidizing agents, e.g., $H_2O_2$, can be dispensed with, particularly if the agent according to the invention does not comprise oxidation dye precursors. If the agent according to the invention comprises air-oxidizable oxidation dye precursors or indole or indoline derivatives, oxidizing agents can be dispensed with in such a case without problems. However, it may be desirable under certain circumstances to add hydrogen peroxide or other oxidizing agents to the agents according to the invention to achieve nuances which are lighter than the fibers containing keratin which are to be colored. Oxidizing agents are generally used in an amount of from 0.01 to 6% by weight, based on the application solution. An oxidizing agent preferred for human hair is $H_2O_2$. Mixtures of two or more oxidizing agents, such as, for example, a combination of hydrogen peroxide and peroxodisulfates of alkali metals and alkaline earth metals or of iodide ion sources, such as, for example, alkali metal iodides and hydrogen peroxide or the above-mentioned peroxodisulfates, can also be used. According to the invention, the oxidizing agent or the oxidizing agent combination can be used in combination with oxidation catalysts in the hair colorant. Oxidation catalysts are, for example, metal salts, metal chelate complexes or metal oxides which permit the metal ions to readily alternate between two oxidation states. Examples are salts, chelate complexes or oxides of iron, ruthenium, manganese and copper. Further possible oxidation catalysts are enzymes. Suitable enzymes are, for example, peroxidases, which can considerably enhance the effect of small amounts of hydrogen peroxide. Also suitable according to the invention are those enzymes which directly oxidize the oxidation dye precursors with the help of atmospheric oxygen, such as, for example, the laccases, or in situ produce small amounts of hydrogen peroxide and, in so doing, biocatalytically activate the oxidation of the dye precursors. Particularly suitable catalysts for the oxidation of the dye precursors are the so-called 2-electron oxidoreductases in combination with the substrates specific therefor, e.g.

pyranose oxidase and e.g., D-glucose or galactose, glucose oxidase and D-glucose, glycerol oxidase and glycerol, pyruvate oxidase and pyruvic acid or salts thereof, alcohol oxidase and alcohol (MeOH, EtOH), lactate oxidase and lactic acid and salts thereof, tyrosinase oxidase and tyrosine, uricase and uric acid or salts thereof, choline oxidase and choline, amino acid oxidase and amino acids.

The colorants according to the invention produce intense colorations even at physiologically compatible temperatures of below 45° C. They are therefore particularly suitable for coloring human hair. For use on human hair, the colorants can usually be incorporated into a hydrous cosmetic carrier. Suitable hydrous cosmetic carriers are, for example, creams, emulsions, gels, or surfactant-containing foaming solutions, such as, for example, shampoos or other preparations which are suitable for application to the fibers containing keratin. If required, it is also possible to incorporate the colorants into anhydrous carriers.

In addition, the colorants according to the invention can comprise all active ingredients, additives and auxiliaries known in such preparations. In many cases, the colorants comprise at least one surfactant, with both anionic and also zwitterionic, ampholytic, nonionic and cationic surfactants being suitable in principle. In many cases, it has, however, proven to be advantageous to choose the surfactants from anionic, zwitterionic or nonionic surfactants.

Suitable anionic surfactants in preparations according to the invention are all anionic surface-active substances suitable for use on the human body. These are characterized by a water-solubilizing, anionic group, such as, for example, a carboxylate, sulfate, sulfonate or phosphate group, and a lipophilic alkyl group having about 10 to 22 carbon atoms. In addition, glycol or polyglycol ether groups, ester groups, ether groups and amide groups and also hydroxyl groups, may be present in the molecule. Examples of suitable anionic surfactants are, in each case in the form of the sodium, potassium and ammonium and also the mono-, di- and trialkanolammonium salts having 2 or 3 carbon atoms in the alkanol group, linear fatty acids having 10 to 22 carbon atoms (soaps),
ether carboxylic acids of the formula R—O—($CH_2$-$CH_2O)_x$—$CH_2$—COOH, in which R is a linear alkyl group having 10 to 22 carbon atoms and x=0 or 1 to 16,
acyl sarcoside having 10 to 18 carbon atoms in the acyl group,
acyl taurides having 10 to 18 carbon atoms in the acyl group,
acyl isethionates having 10 to 18 carbon atoms in the acyl group,
sulfosuccinic mono- and dialkyl esters having 8 to 18 carbon atoms in the alkyl group and sulfosuccinic monoalkylpolyoxyethyl esters having 8 to 18 carbon atoms in the alkyl group and 1 to 6 oxyethyl groups,
linear alkanesulfonates having 12 to 18 carbon atoms,
linear alpha-olefin sulfonates having 12 to 18 carbon atoms,
alpha-sulfo fatty acid methyl esters of fatty acids having 12 to 18 carbon atoms,
alkyl sulfates and alkylpolyglycol ether sulfates of the formula R—O($CH_2$-$CH_2O)_x$—$SO_3$H, in which R is a preferably linear alkyl group having 10 to 18 carbon atoms and x=0 or 1 to 12,
mixtures of surface-active hydroxysulfonates according to DE-A-37 25 030,
sulfonated hydroxyalkyl polyethylene and/or hydroxyalkylene propylene glycol ethers according to DE-A-37 23 354,
sulfonates of unsaturated fatty acids having 12 to 24 carbon atoms and 1 to 6 double bonds according to DE-A-39 26 344,
esters of tartaric acid and citric acid with alcohols, which constitute addition products of about 2 to 15 molecules of ethylene oxide and/or propylene oxide onto fatty alcohols having 8 to 22 carbon atoms.

Preferred anionic surfactants are alkyl sulfate, alkyl polyglycol ether sulfates and ether carboxylic acids having 10 to 18 carbon atoms in the alkyl group and up to 12 glycol ether groups in the molecule, and in particular, salts of saturated and in particular, unsaturated $C_8$–$C_{22}$-carboxylic acids, such as oleic acid, stearic acid, isostearic acid and palmitic acid.

Zwitterionic surfactants is the term used to refer to those surface-active compounds which carry at least one quaternary ammonium group and at least one —COO$^{(-)}$ or —$SO_3^{(-)}$ group. Particularly suitable zwitterionic surfactants are the so-called betaines, such as the N-alkyl-N,N-dimethylammonium glycinates, for example, cocoalkyl dimethylammonium glycinate, N-acylaminopropyl-N,N-dimethylammonium glycinates, for example, cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethyl glycinate. A preferred zwitterionic surfactant is the fatty acid amide derivative known under the CTFA name Cocamidopropyl Betaine.

Ampholytic surfactants are understood as meaning those surface-active compounds which, apart from a $C_{8-18}$-alkyl or -acyl group in the molecule, contain at least one free amino group and at least one —COOH or —$SO_3$H group and are capable of forming internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12-18}$-acylsarcosine.

Nonionic surfactants contain, as hydrophilic group, e.g., a polyol group, a polyalkylene glycol ether group or a combination of polyol and polyglycol ether group. Such compounds are, for example,
addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group,
$C_{12-22}$ fatty acid mono- and diesters of addition products of from 1 to 30 mol of ethylene oxide onto glycerol,
$C_{8-22}$-alkyl mono- and oligoglycosides and ethoxylated analogs thereof,
addition products of from 5 to 60 mol of ethylene oxide onto castor oil and hydrogenated castor oil,
addition products of ethylene oxide onto sorbitan fatty acid esters
addition products of ethylene oxide onto fatty acid alkanolamides.

Examples of the cationic surfactants which can be used in the hair-treatment agents according to the invention are, in particular, quaternary ammonium compounds. Preference is given to ammonium halides, such as alkyltrimethylammonium chlorides, dialkyldimethylammonium chlorides, and trialkylmethylammonium chlorides, e.g., cetyltrimethylammonium chloride, stearyltrimethylammonium chloride, distearyldimethylammonium chloride, lauryidimethylammonium chloride, lauryldimethylbenzylammonium chloride and tricetylmethylammonium chloride. Further cationic surfactants which can be used according to the invention are the quaternized protein hydrolysates.

Likewise suitable according to the invention are cationic silicone oils, such as, for example, the commercially available products Q2-7224 (manufacturer: Dow Corning; a stabilized trimethylsilylamodimethicone), Dow Corning 929 Emulsion (comprising a hydroxylamino-modified silicone, which is also referred to as amodimethicone), SM-2059 (manufacturer: General Electric), SLM-55067 (manufacturer: Wacker), and Abil®-Quat 3270 and 3272 (manufacturer: Th. Goldschmidt; diquaternary polydimethylsiloxanes, quaternium-80).

Alkylamidoamines, in particular, fatty acid amidoamines, such as the stearylamidopropyidimethylamine obtainable under the name Tego Amid®S 18, are characterized not only by a good conditioning effect but specifically by their good biodegradability.

Likewise of very good biodegradability are quaternary ester compounds, so-called "ester quats", such as the methylhydroxyalkyldialkoyloxyalkylammonium methosulflates sold under the trade name Stepantex®.

One example of a quaternary sugar derivative which can be used as cationic surfactant is the commercial product Glucquat® 100, according to CTFA nomenclature a "Lauryl Methyl Gluceth-10 Hydroxpropyl Dimonium Chloride".

The compounds with alkyl groups used as surfactants may in each case be uniform substances. However, it is usually preferred, when manufacturing these substances, to start from native vegetable or animal raw materials, thus giving rise to mixtures of substances with different alkyl chain lengths which depend on the particular raw material.

In the case of surfactants which constitute addition products of ethylene oxide and/or propylene oxide onto fatty alcohols or derivatives of these addition products, it is possible to use either products with a "normal" homolog distribution or those with a narrowed homolog distribution. In this connection, "normal" homolog distribution is understood as meaning mixtures of homologs which are obtained during the reaction of fatty alcohol and alkylene oxide using alkali metals, alkali metal hydroxides or alkali metal alkoxides as catalysts. Narrowed homolog distributions are, by contrast, obtained if, for example, hydrotalcites, alkaline earth metal salts of ether carboxylic acids, alkaline earth metal oxides, hydroxides or alkoxides are used as catalysts. The use of products with a narrowed homolog distribution may be preferred.

Further active ingredients, auxiliaries and additives are, for example,

- nonanionic polymers, such as, for example, vinylpyrrolidione/vinyl acrylate copolymers, polyvinylpyrrolidone and vinylpyrrolidone/vinyl acetate copolymers and polysiloxanes,
- cationic polymers, such as quaternized cellulose ethers, polysiloxanes with quaternary groups, dimethyldiallylammonium chloride polymers, acrylamide-dimethyldiallylammonium chloride copolymers, dimethylaminoethyl methacrylate-vinylpyrrolidione copolymers quaternized with diethyl sulfate, vinylpyrrolidone-imidazolinium methochloride copolymers and quaternized polyvinyl alcohol,
- zwitterionic and amphoteric polymers, such as, for example, acrylamidopropyltrimethylammonium chloride/acrylate copolymers and octylacrylamide/methyl methacrylate/tert-butylaminoethyl methacrylate/2-hydroxypropyl methacrylate copolymers,
- anionic polymers, such as, for example, polyacrylic acids, crosslinked polyacrylic acids, acrylic acid/$C_{10}$–$C_{30}$-alkyl acrylate copolymers, vinyl acetate/crotonic acid copolymers, vinylpyrrolidione/vinyl acrylate copolymers, vinyl acetate/butyl maleate/isobornyl acrylate copolyers, methyl vinyl ether/maleic anhydride copolymers and acrylic acid/ethyl acrylate/N-tert-butyacrylamide terpolymers,
- thickeners, such as agar-agar, guar gum, alginates, xanthan gum, gum Arabic, karaya gum, carob seed flower, linseed gums, dextrans, cellulose derivatives, e.g., methylcellulose, hydroxyalkylcellulose and carboxymethylcellulose, starch fractions and derivatives, such as amylose, amylopectin and dextrins, clays, such as, for example, bentonite or completely synthetic hydrocolloids, such as, for example, polyvinyl alcohol,
- structurants, such as glucose and maleic acid,
- hair-conditioning compounds, such as phospholipids, for example, soya lecithin, egg lecithin and cephalins, and silicone oils,
- protein hydrolysates, in particular, elastin, collagen, keratin, milk protein, soya protein and wheat protein hydrolysates, condensation products thereof with fatty acids, and quaternized protein hydrolysates,
- perfume oils, dimethyl isosorbide and cyclodextrins,
- solubility promoters, such as ethanol, isopropanol, ethylene glycol, propylene glycol, glycerol and diethylene glycol,
- antidandruff active ingredients, such as piroctone olamine and zinc omadine,
- further substances for adjusting the pH,
- active ingredients, such as panthenol, pantothenoic acid, allantoin, pyrrolidonecarboxylic acids and salts thereof, plant extracts and vitamins,
- cholesterol,
- photoprotective agents,
- consistency regulators, such as sugar esters, polyol esters or polyol alkyl ethers,
- fats and waxes, such as spermaceti, beeswax, montan wax, paraffins, fatty alcohols and fatty acid esters,
- fatty acid alkanolamides,
- complexing agents, such as EDTA, NTA and phosphonic acids,
- swelling and penetration substances, such as glycerol, propylene glycol monoethyl ether, carbonates, hydrogen carbonates, guanidines, ureas, and primary, secondary and tertiary phosphates, imidazoles, tannins, pyrrole,
- opacifiers, such as latex,
- pearlizing agents, such as ethylene glycol mono- and distearate,
- propellants, such as propane/butane mixtures, $N_2O$, dimethyl ether, $CO_2$ and air, and
- antioxidants.

The constituents of the hydrous carrier are used for producing the colorants according to the invention in amounts customary for this purpose; e.g., emulsifiers are used in concentrations of from 0.5 to 30% by weight and thickeners are used in concentrations of from 0.1 to 25% by weight, of the total colorant.

For the coloring result, it may be advantageous to add ammonium or metal salts to the colorants. Suitable metal salts are, for example, formiates, carbonates, halides, sulfates, butyrates, valeriates, capronates, acetates, lactates, glycolates, tartrates, citrates, gluconates, propionates, phosphates and phosphonates of alkali metals, such as potassium, sodium or lithium, alkaline earth metals, such as magnesium, calcium, strontium or barium, or of aluminum, manganese, iron, cobalt, copper or zinc, where sodium acetate, lithium bromide, calcium bromide, calcium gluconate, zinc chloride, zinc sulfate, magnesium chloride, magnesium sulfate, ammonium carbonate, ammonium chloride and ammonium acetate are preferred. These salts are preferably present in an amount of from 0.03 to 65 mmol, in particular, from 1 to 40 mmol, based on 100 g of the total colorant.

The pH of the ready-to-use coloring preparations is usually between 2 and 11, preferably between 5 and 10.

The invention secondly provides colorants for fibers containing keratin, in particular, human hair, which reaction products RP according to formula VIII as color-imparting component,

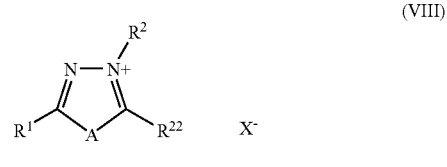

(VIII)

in which
R$^1$, R$^2$, A and X$^-$ are defined as described under formula I,
R$^{22}$ is a group according to formula IX,

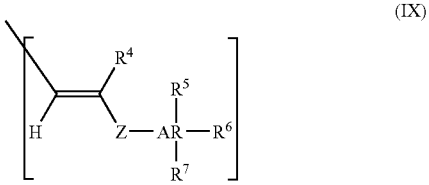

in which
R$^4$, R$^5$, R$^6$, R$^7$, AR and Z are defined as described under formula II.

It is particularly preferred if the agents according to the invention comprise those reaction products RP according to formula VIII in which AR according to formula IX is benzene or naphthalene.

In addition, it is particularly preferred if the agents according to the invention comprise those reaction products RP according to formula VIII in which Z according to formula IX is a direct bond or vinylene.

It is particularly preferred if the agents according to the invention comprise those reaction products RP according to formula VIII in which R$^4$ according to formula IX is a hydrogen atom.

Particularly preferred reaction products RP of this embodiment are selected from 3-ethyl-2-[2-(2-hydroxphenyl)ethenyl]-5-methyl-1,3,4-thiadiazolium tetrafluoroborate, chloride, bromide, 3-allyl-2-[2-(2-hydroxyphenyl)ethenyl]-5-methyl-1,3,4-thiadiazolium tetrafluoroborate, chloride, bromide, 2-[2-(2,3-dihydroxyphenyl)ethenyl]-3-ethyl-5-methyl-1,3,4-thiadiazolium chloride, 2-[2-(2,4-dihydroxyphenyl)ethenyl]-3-ethyl-5-methyl-1,3,4-thiadiazolium bromide, 2-[2-(2,5-dihydroxyphenyl)ethenyl]-3-ethyl-5-methyl-1,3,4-thiadiazolium bromide, 2-[2-(3,4-dihydroxyphenyl)ethenyl]-3-ethyl-5-methyl-1,3,4-thiadiazolium tetrafluoroborate, 3-allyl-2-[2-(2,3-dihydroxyphenyl)ethenyl]-5-methyl-1,3,4-thiadiazolium chloride, 3-allyl-2-[2-(2,4-dihydroxyphenyl)ethenyl]-5-methyl-1,3,4-thiadiazolium bromide, 3-allyl-2-[2-(2,5-dihydroxyphenyl)ethenyl]-5-methyl-1,3,4-thiadiazolium bromide, 3-allyl-2-[2-(3,4-dihydroxyphenyl)ethenyl]5-methyl-1,3,4-thiadiazolium tetrafluoroborate, 3-ethyl-2-[2-(2,3,4-trihydroxyphenyl)ethenyl]-5-methyl-1,3,4-thiadiazolium chloride, 3-ethyl-2-[2-(2,3,5-trihydroxyphenyl)ethenyl]-5-methyl-1,3,4-thiadiazolium tetrafluoroborate, 3-ethyl-2-[2-(2,4,6-trihydroxyphenyl)ethenyl]-5-methyl-1,3,4-thiadiazolium tetrafluoroborate, 3-ethyl-2-[2-(2,3,6-trihydrophenyl)ethenyl]-5-methyl-1,3,4-thiadiazolium bromide, 3-allyl-2-[2-(2,3,4-trihydroxyphenyl)ethenyl]-5-methyl-1,3,4-thiadiazolium bromide, 3-allyl-2-[2-(2,3,5-trihydroxyphenyl)ethenyl]-5-methyl-1,3,4-thiadiazolium bromide, 3-allyl-2-[2-(2,4,6-trihydroxyphenyl)ethenyl]-5-methyl-1,3,4-thiadiazolium tetrafluoroborate, 3-allyl-2-[2-(2,3,6-trihydroxyphenyl)ethenyl]-5-methyl-1,3,4-thiadiazolium bromide, 2-[2-(2,3-dimethoxyphenyl)ethenyl]-3-ethyl-5-methyl-1,3,4-thiadiazolium tetrafluoroborate, 2-[2-(2,4-dimethoxyphenyl)ethenyl]-3-ethyl-5-methyl-1,3,4-thiadiazolium chloride, 2-[2-(2,5-dimethoxyphenyl)ethenyl]-3-ethyl-5-methyl-1,3,4-thiadiazolium tetrafluoroborate, 2-[2-(2,6-dimethoxyphenyl)ethenyl]-3-ethyl-5-methyl-1,3,4-thiadiazolium bromide, 2-[2-(3,4-dimethoxyphenyl)ethenyl]-3-ethyl-5-methyl-1,3,4-thiadiazolium tetrafluoroborate, 3-allyl-2-[2-(2,3-dimethoxyphenyl)ethenyl]-5-methyl-1,3,4-thiadiazolium tetrafluoroborate, 3-allyl-2-[2-(2,4-dimethoxyphenyl)ethenyl]-5-methyl-1,3,4-thiadiazolium chloride, 3-allyl-2-[2-(2,5-dimethoxyphenyl)ethenyl]-5-methyl-1,3,4-thiadiazolium tetrafluoroborate, 3-allyl-2-[2-(2,6-dimethoxyphenyl)ethenyl]-5-methyl-1,3,4-thiadiazolium bromide, 3-allyl-2-[2-(3,4-dimethoxyphenyl)ethenyl]-5-methyl-1,3,4-thiadiazolium tetrafluoroborate, 3-ethyl-2-[2-(2,3,4-trimethoxyphenyl)ethenyl]-5-methyl-1,3,4-thiadiazolium tetrafluoroborate, 3-ethyl-2-[2-(2,3,5-trimethoxyphenyl)ethenyl]-5-methyl-1,3,4-thiadiazolium chloride, 3-ethyl-2-[2-(2,4,6-trimethoxyphenyl)ethenyl-5-methyl-1,3,4-thiadiazolium tetrafluoroborate, 3-allyl-2-[2-(2,3,4-trimethoxyphenyl)ethenyl]-5-methyl-1,3,4-thiadiazolium tetrafluoroborate, 3-allyl-2-[2-(2,3,5-trimethoxyphenyl)ethenyl]-5-methyl-1,3,4-thiadiazolium chloride, 3-allyl-2-[2-(2,4,6-trimethoxyphenyl)ethenyl]5-methyl-1,3,4-thiadiazolium tetrafluoroborate, 3-ethyl-2-[2-(2-hydroxy-3-methoxyphenyl)ethenyl]-5-methyl-1,3,4-thiadiazoliumbromide, 3-ethyl-2-[2-(2-hydroxy-4-methoxyphenyl)ethenyl]-5-methyl-1,3,4-thiadiazolium tetrafluoroborate, 3-ethyl-2-[2-(2-hydroxy-5-methoxyphenyl)ethenyl]-5-methyl-1,3,4-thiadiazolium bromide, 3-ethyl-2-[2-(2-hydroxy-6-methoxyphenyl)ethenyl]-5-methyl-1,3,4-thiadiazolium chloride, 3-ethyl-2-[2-(3-hydroxy-2-methoxyphenyl)ethenyl]-5-methyl-1,3,4-thiadiazolium bromide, 3-ethyl-2-[2-(3-hydroxy-4-methoxyphenyl)ethenyl]-5-methyl-1,3,4-thiadiazolium tetrafluoroborate, 3-ethyl-2-[2-(3-hydroxy-5-methoxyphenyl)ethenyl]-5-methyl-1,3,4-thiadiazolium bromide, 3-ethyl-2-[2-(3-hydroxy-6-methoxyphenyl)ethenyl]-5-methyl-1,3,4-thiadiazolium tetrafluoroborate, 3-ethyl-2-[2-(4-hydroxy-2-methoxyphenyl)ethenyl]-5-methyl-1,3,4-thiadiazolium bromide, 3-ethyl-2-[2-(4-hydroxy-3-methoxyphenyl)ethenyl]-5-methyl-1,3,4-thiadiazolium bromide, 3-allyl-2-[2-(2-hydroxy-3-methoxyphenyl)ethenyl]-5-methyl-1,3,4-thiadiazolium bromide, 3-allyl-2-[2-(2-hydroxy-4-methoxyphenyl)ethenyl]-5-methyl-1,3,4-thiadiazolium bromide, 3-allyl-2-[2-(2-hydroxy-5-methoxyphenyl)ethenyl]-5-methyl-1,3,4-thiadiazolium bromide, 3-allyl-2-[2-(2-hydroxy-6-methoxyphenyl)ethenyl]-5-methyl-1,3,4-thiadiazolium chloride, 3-allyl-2-[2-(3-hydroxy-2-methoxyphenyl)ethenyl]-5-methyl-1,3,4-thiadiazolium bromide, 3-allyl-2-[2-(3-hydroxy-4-methoxyphenyl)ethenyl]-5-methyl-1,3,4-thiadiazolium chloride, 3-allyl-2-[2-(3-hydroxy-5-methoxyphenyl)ethenyl]-5-methyl-1,3,4-thiadiazolium bromide, 3-allyl-2-[2-(3-hydroxy-6-methoxyphenyl)ethenyl]-5-methyl-1,3,4-thiadiazolium bromide, 3-allyl-2-[2-(4-hydroxy-2-methoxyphenyl)ethenyl]-5-methyl-1,3,4-thiadiazolium bromide, 3-allyl-2-[2-(4-hydroxy-3-methoxyphenyl)ethenyl]-5-methyl-1,3,4-thiadiazolium bromide, 3-ethyl-2-[2-(4-hydroxy-3,5-dimethoxyphenyl)ethenyl]-5-methyl-1,3,4-thiadiazolium bromide, 3-allyl-2-[2-(4-hydroxy-3,5-dimethoxyphenyl)ethenyl]-5-methyl-1,3,4-thiadiazolium bromide, 3-ethyl-2-[2-(4-hydroxy-3,5-dimethylphenyl)ethenyl]-5-methyl-1,3,4-thiadiazolium bromide, 3-allyl-2-[2-(4-hydroxy-3,5-dimethylphenyl)ethenyl]-5-methyl-1,3,4-thiadiazolium bromide, 3-ethyl-2-[2-(4-hydroxynaphalen-1-yl)ethenyl]-5-methyl-1,3,4-thiadiazolium bromide, 3-ethyl-2-[2-(2-hydroxynaphalen-1-yl)ethenyl]-5-methyl-1,3,4-thiadiazolium bromide, 3-ethyl-2-[2-(4-methoxynaphalen-1-yl)ethenyl]-5-methyl-1,3,4-thiadiazolium bromide, 3-ethyl-2-[2-(2-methoxynaphalen-1-yl)ethenyl]-5-methyl-1,3,4-thiadiazolium bromide, 3-allyl-2-[2-(4-hydroxynaphalen-1-yl)ethenyl]-5-methyl-1,3,4-thiadiazolium bromide, 3-allyl-2-[2-(2-hydroxynaphalen-1-yl)ethenyl]-5-methyl-1,3,4-thiadiazolium bromide, 3-allyl-2-[2-(4-methoxynaphalen-1-yl)ethenyl]-5-methyl-1,3,4-thiadiazolium bromide, 2-[2-(4-diethylamino-2-hydroxyphenyl)ethenyl]-3-ethyl-5-methyl-1,3,4-thiadiazolium tetrafluoroborate, 3-allyl-2-[2-(4-diethylamino-2-hydroxyphenyl)ethenyl]-5-methyl-1,3,4-thiadiazolium bromide, 2-[2-(4-diethylamino-2-hydroxyphenyl)ethenyl]-3-ethyl-5-methyl-1,3,4-thiadiazolium tetrafluoroborate and 3-allyl-2-[2-(4-dimethylamino-2-hydroxyphenyl)ethenyl]-5-methyl-1,3,4-thiadiazolium bromide.

The reaction product RP is preferably present in the agents in an amount of from 0.03 to 65 mmol, in particular, from 1 to 40 mmol, based on 100 g of the total colorant.

These colorants can additionally comprise
a) at least one of the other above-mentioned direct dyes and/or
b) at least one above-mentioned oxidation dye precursor and/or at least one above-mentioned derivative of indoline or indole, and
c) optionally oxidizing agents, such as, for example, hydrogen peroxide.

In addition, all surfactants, color enhancers, metal salts or oxidizing agents, and all further auxiliaries, active ingredients and additives which have already been specified above may be present in the agent according to the invention of the second subject-matter of the invention.

The present invention thirdly provides the use of at least one compound according to formula I and/or enamine form thereof,

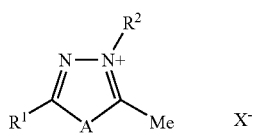

(I)

where $R^1$, $R^2$, A and $X^-$ are as defined above, in combination with at least one reactive carbonyl compound (component B) as coloring component in hair colorants.

In a preferred embodiment, the compounds according to formula I are used in combination with at least one reactive carbonyl compound of component B selected from the above-mentioned preferred and particularly preferred representatives as coloring component in hair colorants.

Moreover, it may be preferred to use at least one reaction product RP of a compound according to formula I and a compound of component B as coloring components in hair colorants.

The present invention fourthly provides a method of coloring fibers containing keratin, in particular, human hair, in which a colorant comprising at least one compound according to formula I and/or enamine form thereof,

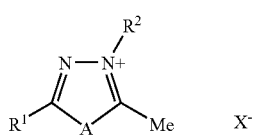

(I)

where $R^1$, $R^2$, A and $X^-$ are as defined above, in combination with at least one compound with a reactive carbonyl group (component B), and customary cosmetic ingredients, is applied to the fibers containing keratin, left on the fibers for a certain time, usually about 15–30 minutes, and is then rinsed out again or washed out with a shampoo. During the contact time of the agent on the fibers, it may be advantageous to assist the coloring process by introducing heat. Heat can be introduced through an external heat source, such as, for example, warm air from a hot-air fan, or, particularly in the case of hair coloration on a living subject, through the body temperature of the subject. In the case of the latter option, the area to be colored is usually covered with a cap.

Here, the compounds according to formula I and the compounds of component B, especially their preferred and particularly preferred representatives specified above, can be applied to the hair as color-imparting components either simultaneously or successively, i.e. in a multistage process, in which case it is unimportant which of the components is applied first. The optionally present ammonium or metal salts can here be added to the compounds with the formula I or the compounds of component B. There may be an interval of up to 30 minutes between the application of the individual components. A pretreatment of the fibers with the salt solution is also possible.

Prior to using the agent according to the invention in the method according to the invention, it may be desirable to subject the fibers containing keratin to be colored to a pretreatment. The order of the pretreatment step required for this and the application of the agent according to the invention does not have to be directly successive, there may instead be a period of up to at most two weeks between the pretreatment step and the application of the agent according to the invention. Several pretreatment methods are suitable for this purpose. Preferably, the fiber is subjected P1 to bleaching before applying the agent according to the invention or P2 to oxidative coloring before applying the agent according to the invention.

In the course of the pretreatment P1, the fiber containing keratin is treated with a bleaching agent. Besides an oxidizing agent, such as customarily hydrogen peroxide, the bleaching agent preferably comprises at least one inorganic persalt which acts as oxidation and bleaching enhancer, such as, for example, a peroxodisulfate of sodium, potassium or ammonium. Colorations according to the method according to the invention through the pretreatment P1 are given a particular brilliance and depth of color.

In the course of the pretreatment P2, an agent comprising the above-mentioned oxidation dye precursors as developer component and optionally coupler component, and optionally the above-mentioned derivatives of indole and/or indoline is applied to the fibers and, after a contact time, optionally with the addition of the above-mentioned suitable oxidizing agents to the hair, is left for 5–45 minutes on the keratin fibers. The hair is then rinsed. By subsequently applying the agent according to the invention, a new color nuance can be imparted to existing oxidation colorations. If the color nuance of the agent according to the invention chosen is the same color nuance of the oxidative coloration, then the coloration of existing oxidation colorations can be freshened up by the method according to the invention. It has been found that freshening up the color or nuancing according to the method according to the invention for freshening up the color or nuancing is on its own superior to conventional direct dyes in terms of the color brilliance and depth of color.

If, besides the compounds according to formula I and optionally component B, the hair colorant additionally comprises, as oxidizing agent, hydrogen peroxide or an oxidizing agent mixture containing hydrogen peroxide, then the pH of the hair colorant containing hydrogen peroxide is preferably in a pH range from pH 7 to pH 11, particularly preferably pH 8 to pH 10. The oxidizing agent can be mixed with the hair colorant directly prior to use and the mixture applied to the hair. If the compounds of the formula I and component B are applied in a two-stage method to the hair, the oxidizing agent is to be applied in one of the two process stages together with the corresponding color-imparting component. For this purpose, it may be preferred to formulate the oxidizing agent with one of the color-imparting components in a container.

The compounds according to formula I and the compounds of component B can either be stored separately or together, either in a liquid to pasty preparation (hydrous or anhydrous) or as dry powder. If the components are stored together in a liquid preparation, then this should be largely anhydrous to lessen a reaction of the components. In the case of separate storage, the reactive components are only mixed together intimately directly prior to application. In the case of dry storage, prior to application, a defined amount of warm (30° C. to 80° C.) water is usually added and a homogenous mixture is prepared.

The invention fifthly provides the use of at least one compound according to formula I and/or enamine form thereof,

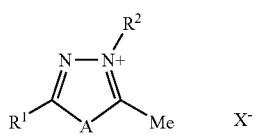

(I)

where $R^1$, $R^2$, A and $X^-$ are as defined above, in combination with reactive carbonyl compounds (component B), for nuancing oxidation colorations of fibers containing keratin, in particular, human hair. During use, it is unimportant whether the nuancing takes place at the same time during the oxidative coloration, or the oxidative coloration precedes the nuancing.

The invention sixthly provides the use of at least one compound according to formula I and/or enamine form thereof,

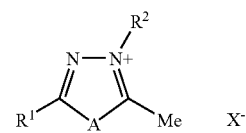

(I)

where $R^1$, $R^2$, A and $X^-$ are as defined above, in combination with at least one reactive carbonyl compound (component B), for freshening up the color of fibers containing keratin which have been colored using oxidative colorants.

As is known, the colorations of fibers containing keratin are exposed to environmental influences, such as, for example, light, rubbing or washes and can, as a result, lose brilliance and depth of color. In the worst case scenario, a nuance shift in the coloration may occur. Such old colorations of fibers containing keratin can, if the user desires, be converted again almost to the colored state as presented itself directly following the original coloration by freshening up the color. It is in accordance with the invention to use a combination of at least one compound of the formula I and at least one reactive carbonyl compound for such a freshening up of color.

EXAMPLES 1.0 Preparation of a Coloring Solution

In each case a slurry or solution of 3 mmol of the compound according to formula I (component A) with 0.41 g of sodium acetate in 30 ml of water was prepared at about 50° C. Directly prior to application, 3 mmol of the compounds of component B are added to this mixture. The mixture was adjusted to a pH of pH 9 using a 10% strength aqueous sodium hydroxide solution (see table 1).

2.0 Colorations

A tress of 90% gray, non-pretreated human hair (Kerling, natural white) was introduced at 30° C. into a freshly prepared coloring solution according to point 1.0 for 30 minutes. The tress was then rinsed with luke warm water for 30 seconds, dried with warm air (30° C. to 40° C.) and then combed.

The respective color nuances and depths of color of the example colorations are shown in table 1 below.

Compounds of Component A (in Table 1):
A1 3-ethyl-2,5-dimethyl-1,3,4-thiadiazolium tetrafluoroborate
A2 2,5-dimethyl-3-(2-propenyl)-1,3,4-thiadiazolium bromide Compounds of Component B (in Table 1):
B1 2,4-dihydroxybenzaldehyde
B2 4-dimethylaminocinnamaldehyde
B3 4-hydroxy-3-methoxybenzaldehyde
B4 4-hydroxy-3-methoxycinnamaldehyde
B5 3,5-dimethoxy-4-hydroxybenzaldehyde
B6 4-hydroxybenzaldehyde
B7 3,5-dimethyl-4-hydroxybenzaldehyde
B8 4-hydroxy-2-methoxybenzaldehyde
B9 3,4-dihydroxybenzaldehyde
B10 2,4,5-trihydroxybenzaldehyde

TABLE 1

| Component A | Component B | Color | pH |
|---|---|---|---|
| A1 | B1 | orange | 9 |
| A1 | B2 | orange-red | 9 |
| A1 | B3 | red | 9 |
| A1 | B4 | brown | 9 |
| A1 | B5 | red-brown | 9 |
| A2 | B1 | orange | 9 |
| A2 | B3 | red | 9 |
| A2 | B4 | medium brown | 9 |
| A2 | B5 | red-brown | 9 |
| A2 | B6 | luminous orange | 9 |
| A2 | B7 | pale red | 9 |
| A2 | B8 | orange | 9 |
| A2 | B9 | dark red | 9 |
| A2 | B10 | pale yellow | 9 |

The invention claimed is:

1. An agent for coloring fibers containing keratin, in particular, human hair, comprising, as component A, at least one compound according to formula I and/or enamine form thereof,

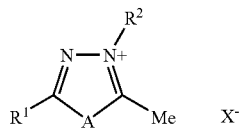

(I)

where
- $R^1$ is a hydrogen atom, a hydroxy group, a mercapto group, a linear or cyclic $C_1$–$C_6$-alkyl group, a $C_2$–$C_6$-alkenyl group, an optionally substituted aryl group, an optionally substituted heteroaryl group, an aryl-$C_1$–$C_6$-alkyl group, a $C_1$–$C_6$-hydroxyalkyl group, a $C_2$–$C_6$-polyhydroxyalkyl group, a $C_1$–$C_6$-alkoxy-$C_2$–$C_6$-alkyl group, a $C_1$–$C_6$-sulfoalkyl group, a $C_1$–$C_6$-carboxyalkyl group, a group $R^I R^{II} N$—$(CH_2)_m$—, in which $R^I$ and $R^{II}$, independently of one another, are a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group, where $R^I$ and $R^{II}$, together with the nitrogen atom, can form a 5-, 6- or 7-membered ring and m is a number 0, 1, 2, 3 or 4,
- $R^2$ is a linear or cyclic $C_1$–$C_6$-alkyl group, a $C_2$–$C_6$-alkenyl group, an optionally substituted aryl group, an optionally substituted heteroaryl group, an aryl-$C_1$–$C_6$-alkyl group, a $C_1$–$C_6$-hydroxyalkyl group, a $C_2$–$C_6$-polyhydroxyalkyl group, a $C_1$–$C_6$-sulfoalkyl group, a $C_1$–$C_6$-carboxyalkyl group, a group $R^{III} R^{IV} N$—$(CH_2)_q$—, in which $R^{III}$ and $R^{IV}$, independently of one another, are a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group and q is a number 1, 2, 3 or 4,
- A is an oxygen atom, a sulfur atom or a group N—R, in which R is a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group,
- $X^-$ is a physiologically compatible anion, and, as component B, at least one compound with a reactive carbonyl group.

2. The agent as claimed in claim 1, characterized in that radical $R^1$ is a $C_1$–$C_6$-alkyl group.

3. The agent as claimed in claim 1, characterized in that radical $R^2$ is selected from the group consisting of a $C_1$–$C_6$-alkyl group, a $C_1$–$C_6$-hydroxyalkyl group and a $C_2$–$C_6$-alkenyl group.

4. The agent as claimed in claim 1, characterized in that A is selected from the group consisting of an oxygen atom and a sulfur atom.

5. The agent as claimed in claim 1, characterized in that $X^-$ is selected from the group consisting of halide, benzenesulfonate, p-toluenesulfonate, $C_1$–$C_4$-alkanesulfonate, trifluoromethanesulfonate, perchlorate, 0.5 sulfate, hydrogensulfate, tetrafluoroborate, hexafluorophosphate and tetrachlorozincate.

6. The agent as claimed in claim 1, characterized in that the compounds according to formula I are selected from the group consisting of 2-methyl-5-phenyl-3-(phenylmethyl)-1,3,4-thiadiazolium tetrafluoroborate, 2-methyl-5-phenyl-3-(phenylmethyl)-1,3,4-thiadiazolium p-toluenesulfonate, 5-(4-chlorophenyl)-2-methyl-3-phenyl-1,3,4-thiadiazolium tetrafluoroborate, 2-methyl-3-(4-nitrophenyl)-5-phenyl-1,3,4-thiadiazolium tetrafluoroborate, 2,3-dimethyl-5-phenyl-1,3,4-thiadiazolium tetrafluoroborate, 2,3-dimethyl-5-phenyl-1,3,4-thiadiazolium p-toluenesulfonate, 2,5-dimethyl-3-(phenylmethyl)-1,3,4-thiadiazolium bromide, 2,5-dimethyl-3-(phenylmethyl)-1,3,4-thiadiazolium chloride, 2,5-dimethyl-3-hexyl-1,3,4-thiadiazolium iodide, 2,5-dimethyl-3-(2-propenyl)-1,3,4-thiadiazolium bromide, 2,5-dimethyl-3-(2-propenyl)-1,3,4-thiadiazolium tetrafluoroborate, 2,5-dimethyl-3-(2-propenyl)-1,3,4-thiadiazolium p-toluenesulfonate, 3-ethyl-2,5-dimethyl-1,3,4-thiadiazolium bromide, 3-ethyl-2,5-dimethyl-1,3,4-thiadiazolium tetrafluoroborate, 3-ethyl-2,5-dimethyl-1,3,4-thiadiazolium p-toluenesulfonate, 2,5-dimethyl-3-(2-hydroxyethyl)-1,3,4-thiadiazolium bromide, 2,5-dimethyl-3-(2-hydroxyethyl)-1,3,4-thiadiazolium p-toluenesulfonate, 3-ethyl-5-(4-methoxyphenyl)-2-methyl-1,3,4-oxadiazolium iodide, 3-ethyl-2-methyl-5-phenyl-1,3,4-oxadiazolium iodide, 3-ethyl-2-methyl-5-phenyl-1,3,4-oxadiazolium tetrafluoroborate, 2,3-dimethyl-5-phenyl-1,3,4-oxadiazolium tetrafluoroborate, 4,5-dimethyl-1,3-diphenyl-4H-1,2,4-triazolium chloride, 4-ethyl-5-methyl-1,3-diphenyl-4H-1,2,4-triazolium chloride and 4-ethyl-5-methyl-1,3-diphenyl-4H-1,2,4-triazolium p-toluenesulfonate.

7. The agent as claimed in claim 1, characterized in that component B is selected from

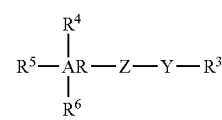

(II)

where
- AR is benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, cinnoline, acridine, julolidine, acenaphthene, fluorene, biphenyl, diphenylmethane, benzophenone, diphenyl ether, azobenzene, chromone, coumarin, diphenylamine, stilbene, where the N-heteroaromatics may also be quaternized,
- $R^3$ is a hydrogen atom, a $C_1$–$C_6$-alkyl group, $C_2$–$C_6$-acyl group, $C_2$–$C_6$-alkenyl group, $C_1$–$C_4$-perfluoroalkyl group, an optionally substituted aryl or heteroaryl group,
- $R^4$, $R^5$ and $R^6$, independently of one another, are a hydrogen atom, a halogen atom, a $C_1$–$C_6$-alkyl group, $C_1$–$C_6$-alkoxy group, $C_1$–$C_6$-aminoalkyl group, $C_1$–$C_6$-hydroxyalkyl group, a $C_1$–$C_6$-alkoxy-$C_1$–$C_6$-alkyloxy group, a $C_2$–$C_6$-acyl group, an acetyl group, carboxyl group, carboxylato group, carbamoyl group, sulfo group, sulfato group, sulfonamide group, sulfonamido group, $C_2$–$C_6$-alkenyl group, an aryl group, an aryl-$C_1$–$C_6$-alkyl group, a hydroxy group, a nitro group, a pyrrolidino group, a morpholino group, a piperidino group, an amino group or ammonio group or a 1-imidazol(in)io group, where the last three groups can be substituted by one or more $C_1$–$C_6$-alkyl groups, $C_1$–$C_6$-carboxyalkyl groups, $C_1$–$C_6$-hydroxyalkyl groups, $C_2$–$C_6$-alkenyl groups, $C_1$–$C_6$-alkoxy-$C_1$–$C_6$-alkyl groups, by optionally substituted benzyl groups, by sulfo-$(C_1$–$C_4)$-alkyl groups or heterocycle-$(C_1$–$C_4)$-alkyl groups, where two of the radicals from $R^4$, $R^5$, $R^6$ and -Z-Y—$R^3$, together with the remainder of the radical, can also form a fused-on optionally substituted 5-, 6- or 7-membered ring, which can likewise carry a fused-on aromatic ring, where the system AR can, depending on the size of the ring, carry further substituents which, independently of one another, can be the same groups as $R^4$, $R^5$ and $R^6$, Z is a direct bond, a carbonyl group, a carboxy-($C_1$–$C_4$)-alkylene group, an optionally substituted $C_2$–$C_6$-alkenylene group, $C_4$–$C_6$-alkadienylene group, furylene group, thienylene group, arylene group, vinylene-arylene group, vinylenefurylene group, vinylenethienylene group, where Z, together with the —Y—$R^3$ group, can also form an optionally substituted 5-, 6- or 7-membered ring, Y is carbonyl group.

8. The agent as claimed in claim 1, characterized in that component B is selected from the group consisting of acetophenone, propiophenone, 2-hydroxyacetophenone, 3-hydroxyacetophenone, 4-hydroxyacetophenone, 2-hydroxypropiophenone, 3-hydroxypropiophenone, 4-hydroxypropiophenone, 2-hydroxybutyrophenone, 3-hydroxybutyrophenone, 4-hydroxybutyrophenone, 2,4-dihydroxyacetophenone, 2,5-dihydroxyacetophenone, 2,6-dihydroxyacetophenone, 2,3,4-trihydroxyacetophenone, 3,4,5-trihydroxyacetophenone, 2,4,6-trihydroxyacetophenone, 2,4,6-trimethoxyacetophenone, 3,4,5-trimethoxyacetophenone, 3,4,5-trimethoxyacetophenone diethyl ketal, 4-hydroxy-3-methoxyacetophenone, 3,5-dimethoxy-4-hydroxyacetophenone, 4-aminoacetophenone, 4-dimethylaminoacetophenone, 4-morpholinoacetophenone, 4-piperidinoacetophenone, 4-imidazolinoacetophenone, 2-hydroxy-5-bromoaoetophenone, 4-hydroxy-3-nitroaoetophenone, acetophenone-2-carboxylic acid, acetophenone-4-carboxylic acid, benzophenone, 4-hydroxybenzophenone, 2-aminobenzophenone, 4,4'-dihydroxybenzophenone, 2,4-dihydroxybenzophenone, 2,4,4'-trihydroxybenzophenone, 2,3,4-trihydroxybenzophenone, 2-hydroxy-1-acetonaphthone, 1-hydroxy-2-acetonaphthone, chromone, chromone-2-carboxylic acid, flavone, 3-hydroxyflavone, 3,5,7-trihydroxyflavone, 4',5,7-trihydroxyflavone, 5,6,7-trihydroxyflavone, quercetin, 1-indanone, 9-fluorenone, 3-hydroxyfluorenone, anthrone, 1,8-dihydroxyanthrone, 1-hydroxy-2-acetonaphthone, chromone, chromone-2-carboxylic acid flavone, 3-hydroxyflavone, 3,5,7-trihydroxyflavone, 4',5,7-trihydroxyflavone, 5,6,7-trihydroxyflavone, quercetin, 1-indanone, 9-fluorenone, 3-hydroxyfluorenone, anthrone, 1,8-dihydroxyanthrone, vanillin, coniferyl aldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,4-dihydroxy-5-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 3,4,5-trihydroxybenzaldehyde, 2,5,6-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde, piperonal, 2,3,6,7-tetrahydro-1H,5H-benzo[ij]quinolizine-9-carboxaldehyde, 2,3,6,7-tetrahydro-8-hydroxy-1H,5H-benzo[ij]quinolizine-9-carboxaldehyde, N-ethylcarbazole-3-aldehyde, 2-formylmethylene-1,3,3-trimethylindoline, 2-indolealdehyde, 3-indolealdehyde, 1-methylindole-3-aldehyde, 2-methylindole-3-aldehyde, 1-acetylindole-3-aldehyde, 3-acetylindole, 1-methyl-3-acetylindole, 2-(1',3',3'-trimethyl-2-indolinylidene)acetaldehyde, 1-methylpyrrole-2-aldehyde, 1-methyl-2-acetylpyrrole, 4-pyridinealdehyde, 2-pyridinealdehyde, 3-pyridinealdehyde, 4-acetylpyridine, 2-acetylpyridine, 3-acetylpyridine, pyridoxal, quinoline-3-aldehyde, quinoline-4-aldehyde, antipyrine-4-aldehyde, furfural, 5-nitrofurfural, 2-thenoyltrifluoroacetone, chromone-3-aldehyde, 3-(5'-nitro-2'-furyl)acrolein, 3-(2'-furyl)acrolein and imidazole-2-aldehyde, 1,3-diacetylbenzene, 1,4-diacetylbenzene, 1,3,5-triacetylbenzene, 2-benzoylacetophenone, 2-(4'-methoxybenzoyl)acetophenone, 2-(2-furoyl)acetophenone, 2-(2'-pyridoyl)acetophenone and 2-(3'-pyridoyl)acetophenone, benzylidene acetone, 4-hydroxybenzylidene acetone, 2-hydroxybenzylidene acetone, 4-methoxybenzylidene acetone, 4-hydroxy-3-methoxybenzylidene acetone, 4-dimethylaminobenzylidene acetone, 3,4-methylenedioxybenzylidene acetone, 4-pyrrolidinobenzylidene acetone, 4-piperidinobenzylidene acetone, 4-morpholinobenzylidene acetone, 4-diethylaminobenzylidene acetone, 3-benzylidene-2,4-pentanedione, 3-(4'-hydroxybenzylidene)-2,4-pentanedione, 3-(4'-dimethylaminobenzylidene)-2,4-pentanedione, 2-benzylidenecyclohexanone, 2-(4'-hydroxybenzylidene)cyclohexanone, 2-(4'-dimethylaminobenzylidene)cyclohexanone, 2-benzylidene-1,3-cyclohexanedione, 2-(4'-hydroxybenzylidene)-1,3-cyclohexanedione, 3-(4'-dimethylaminobenzylidene)-1,3-cyclohexanedione, 2-benzylidene-5,5-dimethyl-1,3-cyclohexanedione, 2-(4'-hydroxybenzylidene)-5,5-dimethyl-1,3-cyclohexanedione, 2-(4'-hydroxy-3-methoxybenzylidene)-5,5-dimethyl-1,3-cyclohexanedione, 2-(4'-dimethylaminobenzylidene)-5,5-dimethyl-1,3-cyclohexanedione, 2-benzylidenecyclopentanone, 2'-(4-hydroxybenzylidene)cyclopentanone, 2-(4'-dimethylaminobenzylidene)cyclopentanone, 5-(4-dimethylaminophenyl)penta-2,4-dienal, 5-(4-diethylaminophenyl)penta-2,4-dienal, 5-(4-methoxyphenyl)penta-2,4-dienal, 5-(3,4-dimethoxyphenyl)penta-2,4-dienal, 5-(2,4-dimethoxyphenyl)penta-2,4-dienal, 5-(4-piperidinophenyl)penta-2,4-dienal morpholinophenyl)penta-2,4-dienal, 5-(4-pyrrolidinophenyl)penta-2,4-dienal, dimethylaminophenyl)hexa-3,5-dien-2-one, 6-(4-diethylaminophenyl)hexa-3,5-dien-2-one, 6-(4-methoxyphenyl)hexa-3,5-dien-2-one, 6-(3,4-dimethoxyphenyl)hexa-3,5-dien-2-one, 6-(2,4-dimethoxyphenyl)hexa-3,5-dien-2-one, 6-(4-piperidinophenyl)hexa-3,5-dien-2-one, 6-(4-morpholinophenyl)hexa-3,5-dien-2-one, 6-(4-pyrrolidinophenyl)hexa-3,5-dien-2-one, 5-(4-dimethylamino-1-naphthyl)penta-3,5-dienal, 2-nitrobenzaldehyde, 3-nitrobenzaldehyde, 4-nitrobenzaldehyde, 4-methyl-3-nitrobenzaldehyde, 3-hydroxy-4-nitrobenzaldehyde, 4-hydroxy-3-nitrobenzaldehyde, 5-hydroxy-2-nitrobenzaldehyde, 2-hydroxy-5-nitrobenzaldehyde, 2-hydroxy-3-nitrobenzaldehyde, 2-fluoro-3-nitrobenzaldehyde, 3-methoxy-2-nitrobenzaldehyde, 4-chloro-3-nitrobenzaldehyde, 2-chloro-6-nitrobenzaldehyde, 5-chloro-2-nitrobenzaldehyde, 4-chloro-2-nitrobenzaldehyde, 2,4-dinitrobenzaldehyde, 2,6-dinitrobenzaldehyde, 2-hydroxy-3-methoxy-5-nitrobenzaldehyde, 4,5-dimethoxy-2-nitrobenzaldehyde, 6-nitropiperonal, 2-nitropiperonal, 5-nitrovanillin, 2,5-dinitrosalicylaldehyde, 5-bromo-3-nitrosalicylaldehyde, 3-nitro-4-formylbenzenesulfonic acid, 4-nitro-1-naphthaldehyde, 2-nitrocinnamaldehyde, 3-nitrocinnamatdehyde, 4-nitrocinnamaldehyde, 9-methyl-3-carbazolealdehyde, 9-ethyl-3-carbazolealdehyde, 3-acetylcarbazole, 3,6-diacetyl-9-ethylcarbazole, 3-acetyl-9-methylcarbazole, 1,4-dimethyl-3-carbazolealdehyde, 1,4,9-trimethyl-3-carbazolealdehyde, 4-formyl-1-methylpyridinium, 2-formyl-1-methylpyridinium, 4-formyl-1-ethylpyridinium, 2-formyl-1-ethylpyridinium, 4-formyl-1-benzylpyridinium, 2-formyl-1-benzylpyridinium, 4-formyl-1,2-dimethylpyridinium, 4-formyl-1,3-dimethylpyridinium, 4-formyl-1-methylquinolinium, 2-formyl-1-methylquinolinium, 4-acetyl-1-methylpyridinium, 2-acetyl-1-methylpyridinium, 4-acetyl-1-methylquinolinium, 5-formyl-1-methylquinolinium, 6-formyl-1-methylquinolinium, 7-formyl-1-methylquinolinium, 8-formyl-1-methylquinolinium, 5-formyl-1-ethylquinolinium, 6-formyl-1-ethylquinolinium, 7-formyl-1-ethylquinolinium, 8-formyl-1-ethylquinolinium, 5-formyl-1-benzylquinolinium, 6-formyl-1-benzylquinolinium, 7-formyl-1-benzylquinolinium, 8-formyl-1-benzylquinolinium, 5-formyl-1-allylquinolinium, 6-formyl-1-allylquinolinium, 7-formyl-1-allylquinolinium and 8-formyl-1-allylquinolinium, 5-acetyl-1-methylquinolinium, 6-acetyl-1-methylquinolinium, 7-acetyl-1-methylquinolinium, 8-acetyl-1-methylquinolinium, 5-acetyl-1-ethylquinolinium, 6-acetyl-1-ethylquinolinium, 7-acetyl-1-ethylquinolinium, 8-acetyl-1-ethylquinolinium, 5-acetyl-1-benzylquinolinium, 6-acetyl-1-benzylquinolinium, 7-acetyl-1-benzylquinolinium, 8-acetyl-1-benzylquinolinium, 5-acetyl-1-allylquinolinium, 6-acetyl-1-allylquinolinium, 7-acetyl-1-allylquinolinium and 8-acetyl-1-allylquinolinium, 9-formyl-10-methylacridinium, 4-(2'-formylvinyl)-1-methylpyridinium, 1,3-dimethyl-2-(4'-formylphenyl)benzimidazolium, 1,3-dimethyl-2-(4'-formylphenyl)imidazolium 2-(4'-formylphenyl)-3-methylbenzothiazolium, acetylphenyl)-3-methylbenzothiazolium, 2-(4'-formylphenyl)-3-methylbenzoxazolium, formyl-2'-furyl)-3-methylbenzothiazolium 2-(5'-formyl-2'-furyl)-3-methylbenzothiazolium 2-(5'-formyl-2'-thienyl)-3-methylbenzothiazolium 2-(3'-formylphenyl)-3-methylbenzothiazolium, 2-(4'-formyl-1-naphthyl)-3-methylbenzothiazolium, 5-chloro-2-(4'-formylphenyl)-3-methylbenzothiazolium, 2-(4'-formylphenyl)-3,5-dimethylbenzothiazolium benzenesulfonate, isatin, 1-methylisatin, 1-allylisatin, 1-hydroxymethylisatin, 5-chloroisatin, 5-methoxyisatin, 5-nitroisatin, 6-nitroisatin, 5-sulfoisatin, 5-carboxyisatin, quinisatin, 1-methylquinisatin, and any mixtures of the above compounds.

9. The agent as claimed in claim 1, characterized in that component B is selected from the group consisting of vanillin, coniferylaldehyde, 2-methoxybenzaldehyde, 3-methoxybenzaldehyde, 4-methoxybenzaldehyde, 2-ethoxybenzaldehyde, 3-ethoxybenzaldehyde, 4-ethoxybenzaldehyde, 4-hydroxy-2,3-dimethoxybenzaldehyde, 4-hydroxy-2,5-dimethoxybenzaldehyde, 4-hydroxy-2,6-dimethoxybenzaldehyde, 4-hydroxy-2-methylbenzaldehyde, 4-hydroxy-3-methylbenzaldehyde, 4-hydroxy-2,3-dimethylbenzaldehyde, 4-hydroxy-2,5-dimethylbenzaldehyde, 4-hydroxy-2,6-dimethylbenzaldehyde, 4-hydroxy-3,5-dimethoxybenzaldehyde, 4-hydroxy-3,5-dimethylbenzaldehyde, 3,5-diethoxy-4-hydroxybenzaldehyde, 2,6-diethoxy-4-hydroxybenzaldehyde, 3-hydroxy-4-methoxybenzaldehyde, 2-hydroxy-4-methoxybenzaldehyde, 2-ethoxy-4-hydroxybenzaldehyde, 3-ethoxy-4-hydroxybenzaldehyde, 4-ethoxy-2-hydroxybenzaldehyde, 4-ethoxy-3-hydroxybenzaldehyde, 2,3-dimethoxybenzaldehyde, 2,4-dimethoxybenzaldehyde, 2,5-dimethoxybenzaldehyde, 2,6-dimethoxybenzaldehyde, 3,4-dimethoxybenzaldehyde, 3,5-dimethoxybenzaldehyde, 2,3,4-trimethoxybenzaldehyde, 2,3,5-trimethoxybenzaldehyde, 2,3,6-trimethoxybenzaldehyde, 2,4,6-trimethoxybenzaldehyde, 2,4,5-trimethoxybenzaldehyde, 2,5,6-trimethoxybenzaldehyde, 2-hydroxybenzaldehyde, 3-hydroxybenzaldehyde, 4-hydroxybenzaldehyde, 2,3-dihydroxybenzaldehyde, 2,4-dihydroxybenzaldehyde, 2,4-dihydroxy-3-methylbenzaldehyde, 2,4-dihydroxy-5-methylbenzaldehyde, 2,4-dihydroxy-6-methylbenzaldehyde, 2,4-dihydroxy-3-methoxybenzaldehyde, 2,4-dihydroxy-5-methoxybenzaldehyde, 2,4-dihydroxy-6-methoxybenzaldehyde, 2,5-dihydroxybenzaldehyde, 2,6-dihydroxybenzaldehyde, 3,4-dihydroxybenzaldehyde, 3,4-dihydroxy-2-methylbenzaldehyde, 3,4-dihydroxy-5-methylbenzaldehyde, 3,4-dihydroxy-6-methylbenzaldehyde, 3,4-dihydroxy-2-methoxybenzaldehyde, 3,4-dihydroxy-5-methoxybenzaldehyde, 3,5-dihydroxybenzaldehyde, 2,3,4-trihydroxybenzaldehyde, 2,3,5-trihydroxybenzaldehyde, 2,3,6-trihydroxybenzaldehyde, 2,4,6-trihydroxybenzaldehyde, 2,4,5-trihydroxybenzaldehyde, 2,5,6-trihydroxybenzaldehyde, 3,4,5-trihydroxybenzaldehyde, 4-hydroxy-2-methoxybenzaldehyde, 4-dimethylaminobenzaldehyde, 4-diethylaminobenzaldehyde, 4-dimethylamino-2-hydroxybenzaldehyde, 4-diethylamino-2-hydroxybenzaldehyde, 4-pyrrolidinobenzaldehyde, 4-morpholinobenzaldehyde, 2-morpholinobenzaldehyde, 4-piperidinobenzaldehyde, 2-methoxy-1-naphthaldehyde, 4-methoxy-1-naphthaldehyde, 2-hydroxy-1-naphthaldehyde, 2,4-dihydroxy-1-naphthaldehyde, 4-hydroxy-3-methoxy-1-naphthaldehyde, 2-hydroxy-4-methoxy-1-naphthaldehyde, 3-hydroxy-4-methoxy-1-naphthaldehyde, 2,4-dimethoxy-1-naphthaldehyde, 3,4-dimethoxy-1-naphthaldehyde, 4-hydroxy-1-naphthaldehyde, 4-dimethylamino-1-naphthaldehyde, 4-dimethylaminocinnamaldehyde, 2-dimethylaminobenzaldehyde, 2-chloro-4-dimethylaminobenzaldehyde, 4-dimethylamino-2-methylbenzaldehyde, 4-diethylaminocinnamaldehyde, 4-dibutylaminobenzaldehyde, 4-diphenylaminobenzaldehyde, 4-dimethylamino-2-methoxybenzaldehyde, 4-(1-imidazolyl)benzaldehyde and piperonal.

10. The agent as claimed in claim 1, characterized in that it further comprises at least one compound as component C, selected from (a) OH-acidic compounds and (b) compounds with primary or secondary amino or hydroxy groups, selected from the group consisting of aromatic hydroxy compounds, primary or secondary aromatic amines and nitrogen-containing heterocyclic compounds.

11. The agent as claimed in claim 10, characterized in that the CH-acidic compounds of component C are selected from the group consisting of 1,2,3,3-tetramethyl-3H-indolium iodide, 1,2,3,3-tetramethyl-3H-indolium p-toluenesulfonate, 1,2,3,3-tetramethyl-3H-indolium methanesulfonate, 1,3,3-trimethyl-2-methyleneindoline, 2,3-dimethylbenzothiazolium iodide, 2,3-dimethylbenzothiazolium p-toluenesulfonate, 2,3-dimethylnaphtho[1,2-d]thiazolium p-toluenesulfonate, 3-ethyl-2-methylnaphtho[1,2-d]thiazolium p-toluenesulfonate, rhodanine, rhodanine-3-acetic acid, 1,4-dimethylquinolinium iodide, 1,2-dimethylquinolinium iodide, barbituric acid, thiobarbituric acid, 1,3-dimethylthiobarbituric acid, 1,3-diethylthiobarbituric acid, 1,3-diethylbarbituric acid, oxindole, 3-indoxyl acetate, 2-coumaranone, 5-hydroxy-2-coumaranone, 6-hydroxy-2-coumaranone, 3-methyl-1-phenylpyrazolin-5-one, indane-1,2-dione, indane-1,3-dione, indan-1-one, benzoylacetonitrile, 3-dicyanomethyleneindan-1-one, 2-amino-4-imino-1,3-thiazoline hydrochloride, 5,5-dimethylcyclohexane-1,3-dione, 2H-1,4-benzoxazin-4H-3-one, 3-ethyl-2-methylbenzoxazolium iodide, 3-ethyl-2-methylbenzothiazolium iodide, 1-ethyl-4-methyl-quinolinium iodide, 1-ethyl-2-methylquinolinium iodide, 1,2,3-trimethylquinoxalinium iodide, 3-ethyl-2-methylbenzoxazolium p-toluenesulfonate, 3-ethyl-2-methylbenzothiazolium p-toluenesulfonate, 1-ethyl-4-methylquinolinium p-toluenesulfonate, 1-ethyl-2-methylquinolinium p-toluenesulfonate, 1,2,3-trimethylquinoxalinium p-toluenesulfonate, 1,2-dihydro-1,3,4,6-tetramethyl-2-oxopyrimidinium chloride, 1,2-dihydro-1,3,4,6-tetramethyl-2-oxopyrimidinium hydrogensulfate, 1,2-dihydro-1,3,4-trimethyl-2-oxopyrimidinium chloride, 1,2-dihydro-4,6-dimethyl-1,3-dipropyl-2-oxopyrimidinium chloride, 1,2-dihydro-1,3,4,6-tetramethyl-2-thioxopyrimidinium hydrogensulfate and 2-dihydro-1,3,4,5,6-pentamethyl-2-oxopyrimidinium chloride.

12. The agent as claimed in claim 10, characterized in that the primary and secondary aromatic amines of component C are selected from the group consisting of N,N-dimethyl-p-phenylenediamine, N,N-diethyl-p-phenylenediamine, N-(2-hydroxyethyl)-N-ethyl-p-phenylenediamine, N,N-bis(2-hydroxyethyl)-p-phenylenediamine, N-(2-methoxyethyl)-p-phenylenediamine, 2,3-dichloro-p-phenylenediamine, 2,4-dichloro-p-phenylenediamine, 2,5-dichloro-p-phenylenediamine, 2-chloro-p-phenylenediamine, 2,5-dihydroxy-4-morpholinoaniline, 2-aminophenol, 3-aminophenol, 4-aminophenol, 2-aminomethyl-4-aminophenol, 2-hydroxymethyl-4-aminophenol, o-phenylenediamine, m-phenylenediamine, p-phenylenediamine, 2,5-diaminotoluene, 2,5-diaminophenol, 2,5-diaminoanisole, 2,5-diaminophenthol, 4-amino-3-methylphenol, 2-(2,5-diaminophenyl)ethanol, 2,4-diaminophenoxyethanol, 2-(2,5-diaminophenoxy)ethanol, 3-amino-4-(2-hydroxyethyloxy) phenol, 3,4-methylenedioxyphenol, 3,4-methylenedioxyaniline, 3-amino-2,4-dichlorophenol, 4-methylaminophenol, 2-methyl-5-aminophenol, 3-methyl-4-aminophenol, 2-methyl-5-(2-hydroxyethylamino)phenol, 3-amino-2-chloro-6-methylphenol, 2-methyl-5-amino-4-chlorophenol, 5-(2-hydroxyethylamino)-4-methoxy-2-methylphenol, 4-amino-2-hydroxymethylphenol, 2-(diethylaminomethyl)-4-aminophenol, 4-amino-1-hydroxy-2-(2-hydroxyethylaminomethyl)benzene, 1-hydroxy-2-amino-5-methylbenzene, 1-hydroxy-2-amino-6-methylbenzene, 2-amino-5-acetamidophenol, 1,3-dimethyl-2,5-diaminobenzene, 5-(3-hydroxypropylamino)-2-methylphenol, 5-amino-4-methoxy-2-methylphenol, N,N-dimethyl-3-aminophenol, N-cyclopentyl-3-aminophenol, 5-amino-4-fluoro-2-methylphenol, 2,4-diamino-5-fluorotoluene, 2,4-diamino-5-(2-hydroxyethoxy)toluene, 2,4-diamino-5-methylphenetol, 3,5-diamino-2-methoxy-1-methylbenzene, 2-amino-4-(2-hydroxyethylamino)anisole, 2,6-bis(2-hydroxyethylamino)-1-methylbenzene, 1,3-diamino-2,4-dimethoxybenzene, 3,5-diamino-2-methoxytoluene, 2-aminobenzoic acid, 3-aminobenzoic acid, 4-aminobenzoic acid, 2-aminophenylacetic acid, 3-aminophenylacetic acid, 4-aminophenylacetic acid, 2,3-diaminobenzoic acid, 2,4-diaminobenzoic acid, 2,5-diaminobenzoic acid, 3,4-diaminobenzoic acid, 3,5-diaminobenzoic acid, 4-aminosalicylic acid, 5-aminosalicylic acid, 3-amino-4-hydroxybenzoic acid, 4-amino-3-hydroxybenzoic acid, 2-aminobenzenesulfonic acid, 3-aminobenzenesuifonic acid, 4-aminobenzenesulfonic acid, 3-amino-4-hydroxybenzenesulfonic acid, 4-amino-3-hydroxynaphthalene-1-sulfonic acid, 6-amino-7-hydroxynaphthalene-2-sulfonic acid, 7-amino-4-hydroxynaphthalene-2-sulfonic acid, 4-amino-5-hydroxynaphthalene-2,7-disulfonic acid, 3-amino-2-naphthoic acid, 3-aminophthalic acid, 5-aminoisophthalic acid, 1,3,5-triaminobenzene, 1,2,4-triaminobenzene, 1,2,4,5-tetraaminobenzene, 2,4,5-triaminophenol, pentaaminobenzene, hexaaminobenzene, 2,4,6-triaminoresorcinol, 4,5-diaminopyrocatechin, 4,6-diaminopyrogallol, 1-(2-hydroxy-5-aminobenzyl)-2-imidazolidinone, 4-amino-2-((4-[(5-amino-2-4-hydroxyphenyl)methyl]piperazinyl)methyl) phenol, 3,5-diamino-4-hydroxypyrocatechin, 1,4-bis(4-aminophenyl)-1,4-diazacycloheptane, aromatic nitriles, such as 2-amino-4-hydroxybenzonitrile, 4-amino-2-hydroxybenzonitrile, 4-aminobenzonitrile, 2,4-diaminobenzonitrile, amino compounds containing nitro groups, such as 3-amino-6-methylamino-2-nitropyridine, picramic acid, [8-[(4-amino-2-nitrophenyl)azo]-7-hydroxynaphth-2-yl]trimethylammonium chloride, [8-((4-amino-3-nitrophenyl)azo)-7-hydroxynaphth-2-yl]trimethylammonium chloride (Basic Brown 17), 1-hydroxy-2-amino-4,6-dinitrobenzene, 1-amino-2-nitro-4-[bis(2-hydroxyethyl)amino]benzene, 1-amino-2-[(2-hydroxyethyl)amino]-5-nitrobenzene (HC Yellow No. 5), 1-amino-2-nitro-4-[(2-hydroxyethyl)amino] benzene (HC Red No. 7), 2-chloro-5-nitro-N-2-hydroxyethyl-1,4-phenylenediamine, 1-[(2-hydroxyethyl)amino]-2-nitro-4-aminobenzene (HC Red No. 3), 4-amino-3-nitrophenol, 4-amino-2-nitrophenol, 6-nitro-o-toluidine, 1-amino-3-methyl-4-[(2-hydroxyethyl)amino]-6-nitrobenzene (HC Violet No. 1), 1-amino-2-nitro-4-[(2,3-dihydroxypropyl)amino]-5-chlorobenzene (HC Red No. 10), 2-(4-amino-2-nitroanilino)benzoic acid, 6-nitro-2,5-diaminopyridine, 2-amino-6-chloro-4-nitrophenol, 1-amino-2-(3-nitrophenylazo)-7-phenylazo-8-naphthol-3,6- disulfonic acid disodium salt (Acid Blue No. 29), 1-amino-2-(2-hydroxy-4-nitrophenylazo)-8-naphthol-3,6-disulfonic acid disodium salt (palatine chrome green), 1-amino-2-(3-chloro-2-hydroxy-5-nitrophenylazo)-8-naphthol-3,6-disulfonic acid disodium salt (Gallion), 4-amino-4'-nitrostilbene-2,2'-disulfonic acid disodium salt, 2,4-diamino-3',5'-dinitro-2'-hydroxy-5-methylazobenzene (Mordant Brown 4), 4-amino-4-nitrodiphenylamine-2-sulfonic acid, 4'-amino-3-nitrobenzophenone-2-carboxylic acid, 1-amino-4-nitro-2-(2-nitrobenzylideneamino)benzene, 2-[2-(diethylamino)ethylamino]-5-nitroaniline, 3-amino-4-hydroxy-5-nitrobenzenesulfonic acid, 3-amino-3'-nitrobiphenyl, 3-amino-4-nitroacenaphthene, 2-amino-1-nitronaphthalene, 5-amino-6-nitrobenzo-1,3-dioxole, anilines, in particular, anilines containing nitro groups, such as 4-nitroaniline, 2-nitroaniline, 1,4-diamino-2-nitrobenzene, 1,2-diamino-4-nitrobenzene, 1-amino-2-methyl-6-nitrobenzene, 4-nitro-1,3-phenylenediamine, 2-nitro-4-amino-1-(2-hydroxyethylamino)benzene, 2-nitro-1-amino-4-[bis(2-hydroxyethyl)amino]benzene, 4-amino-2-nitrodiphenylamine-2'-carboxylic acid, 1-amino-5-chloro-4-(2-hydroxyethylamino)-2-nitrobenzene, aromatic anilines and phenols with a further aromatic radical as shown in formula (VI)

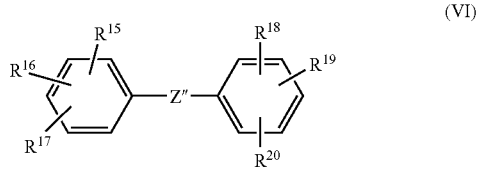

(VI)

in which
R$^{15}$ is a hydroxy or an amino group which may be substituted by C$_1$–C$_6$-alkyl, C$_1$–C$_6$-hydroxyalkyl, C$_1$–C$_6$-alkoxy or C$_1$–C$_6$-alkoxy-C$_1$–C$_6$-alkyl groups,
R$^{16}$, R$^{17}$, R$^{18}$, R$^{19}$ and R$^{20}$, independently of one another, are a hydrogen atom, a hydroxy or an amino group which may be substituted by C$_1$–C$_6$-alkyl, C$_1$–C$_6$-hydroxyalkyl, C$_1$–C$_6$-alkoxy, C$_1$–C$_6$-aminoalkyl or C$_1$–C$_6$-alkoxy-C$_1$–C$_6$-alkyl groups, and
Z" is a direct bond, a saturated or unsaturated carbon chain optionally substituted by hydroxy groups and having 1 to 4 carbon atoms, a carbonyl group, sulfonyl group or imino group, an oxygen atom or sulfur atom, or a group with the formula (VII)

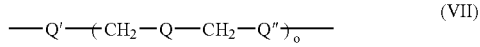

(VII)

in which
Q is a direct bond, a CH$_2$ group or CHOH group,
Q' and Q", independently of one another, are an oxygen atom, an NR$^{21}$ group, in which R$^{21}$ is a hydrogen atom, a C$_1$–C$_6$-alkyl group or C$_1$–C$_6$-hydroxyalkyl group, where also the two groups, together with the remaining molecule, can form a 5-, 6- or 7-membered ring, the group O—(CH$_2$)$_p$—NH or NH—(CH$_2$)$_p$'—O, in which p and p' are 2 or 3, and
o is a number from 1 to 4,
such as, in particular, 4,4'-diaminostilbene and its hydrochloride, 4,4'-diaminostilbene-2,2'-disulfonic acid mono- or di-Na salt, 4-amino-4'-dimethylaminostilbene and its hydrochloride, 4,4'-diaminodiphenylmethane, 4,4'-diaminodiphenyl sulfide, 4,4'-diaminodiphenyl sulfoxide, 4,4'-diaminodiphenylamine, 4,4'-diaminodiphenylamine-2-sulfonic acid, 4,4'-diaminobenzophenone, 4,4'-diaminodiphenyl ether, 3,3',4,4'-tetraaminodiphenyl, 3,3',4,4'-tetraaminobenzophenone, 1,3-bis(2,4-diaminophenoxy)propane, 1,8-bis(2,5-diaminophenoxy)-3,6-dioxaoctane, 1,3-bis(4-aminophenylamino)propane, 1,3-bis(4-aminophenylamino)-2-propanol, 1,3-bis[N-(4-aminophenyl)-2-hydroxyethylamino]-2-propanol, N,N-bis[2-(4-aminophenoxy)ethyl]methylamine, N-phenyl-1,4-phenylenediamine and bis(5-amino-2-hydroxyphenyl)methane.

13. The agent as claimed in claim 10, characterized in that the aromatic hydroxy compounds of component C are selected from the group consisting of 2-methylresorcinol, 4-methylresorcinol, 5-methylresorcinol, 2,5-dimethylresorcinol, resorcinol, 3-methoxyphenol, pyrocatechin, hydroquinone, pyrogallol, phloroglucine, hydroxyhydroquinone, 2-methoxyphenol, 3-methoxyphenol, 4-methoxyphenol, 3-dimethylaminophenol, 2-(2-hydroxyethyl)phenol, 3,4-methylenedioxyphenol, 2,4-dihydroxybenzoic acid, 3,4-dihydroxybenzoic acid, 1-(2,4-dihydroxyphenyl)acetic acid, 1-(3,4-dihydroxyphenyl)acetic acid, gallic acid, 2,4,6-trihydroxybenzoic acid, -acetophenone, 2-chlororesorcinol, 4-chlororesorcinol, 1-naphthol, 1,5-dihydroxynaphthalene, 2,3-dihydroxynaphthalene, 2,7-dihydroxynaphthalene, 6-dimethylamino-4-hydroxy-2-naphthalenesulfonic acid and 3,6-dihydroxy-2,7-naphthalenesulfonic acid.

14. The agent as claimed in claim 10, characterized in that the nitrogen-containing heterocyclic compounds of component C are selected from the group consisting of 2-aminopyridine, 3-aminopyridine, 4-aminopyridine, 2-amino-3-hydroxypyridine, 2,6-diaminopyridine, 2,5-diaminopyridine, 2-(aminoethylamino)-5-aminopyridine, 2,3-diaminopyridine, 2-dimethylamino-5-aminopyridine, 2-methylamino-3-amino-6-methoxypyridine, 2,3-diamino-6-methoxypyridine, 2,6-dimethoxy-3,5-diaminopyridine, 2,4,5-triaminopyridine, 2,6-dihydroxy-3,4-dimethylpyridine, N-[2-(2,4-diaminophenyl)aminoethyl]-N-(5-amino-2-pyridyl)amine, N-[2-(4-aminophenyl)aminoethyl]-N -(5-amino-2-pyridyl)amine, 2,4-dihydroxy-5,6-diaminopyrimidine, 4,5,6-triaminopyrimidine, 4-hydroxy-2,5,6-triaminopyrimidine, 2-hydroxy-4,5,6-triaminopyrimidine, 2,4,5,6-tetraaminopyrimidine, 2-methylamino-4,5,6-triaminopyrimidine, 2,4-diaminopyrimidine, 4,5-diaminopyrimidine, 2-amino-4-methoxy-6-methylpyrimidine, 3,5-diaminopyrazole, 3,5-diamino-1,2,4-triazole, 3-aminopyrazole, 3-amino-5-hydroxypyrazole, 1-phenyl-4,5-diaminopyrazole, 1-(2-hydroxyethyl)-4,5-diaminopyrazole, 1-phenyl-3-methyl-4,5-diaminopyrazole, 4-amino-2,3-dimethyl-1-phenyl-3-pyrazolin-5-one (4-aminoantipyrin), 1-phenyl-3-methylpyrazol-5-one, 2-aminoquinoline, 3-aminoquinoline, 8-aminoquinoline, 4-aminoquinaldine, 2-aminonicotinic acid, 6-aminonicotinic acid, 5-aminoisoquinoline, 5-aminoindazole, 6-aminoindazole, 5-aminobenzimidazole, 7-aminobenzimidazole, 5-aminobenzothiazole, 7-aminobenzothiazole, 2,5-dihydroxy-4-morpholinoaniline, and indole and indoline derivatives, such as 4-aminoindole, 5-aminoindole, 6-aminoindole, 7-aminoindole, 5,6-dihydroxyindole, 4-hydroxyindoline and hydroxypyrimidine derivatives and the physiologically compatible salts of the above-mentioned compounds.

15. A colorant comprising the agent as claimed in claim 10, characterized in that the compounds of the formula I, the compounds of component B and the compounds of component C are each present in an amount of from 0.03 to 65 mmol, based on 100 g of the total colorant.

16. The agent as claimed in claim 1, characterized in that it at least contains one reaction product RP according to formula VIII,

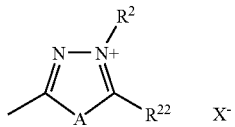
(VIII)

in which
- $R^1$ is a hydrogen atom, a hydroxy group, a mercapto group, a linear or cyclic $C_1$–$C_6$-alkyl group, a $C_2$–$C_6$-alkenyl group, an optionally substituted aryl group, an optionally substituted heteroaryl group, an aryl-$C_1$–$C_6$-alkyl group, a $C_1$–$C_6$-hydroxyalkyl group, a $C_2$–$C_6$-polyhydroxyalkyl group, a $C_1$–$C_6$-alkoxy-$C_2$–$C_6$-alkyl group, a $C_1$–$C_6$-sulfoalkyl group, a $C_1$–$C_6$-carboxyalkyl group, a group $R^IR^{II}N$—$(CH_2)_{m}$-, in which $R^I$ and $R^{II}$, independently of one another, are a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_4$-alkyl group, where $R^I$ and $R^{II}$, together with the nitrogen atom, can form a 5-, 6- or 7-membered ring and m is a number 0, 1, 2, 3 or 4,
- $R^2$ is a linear or cyclic $C_1$–$C_6$-alkyl group, a $C_2$–$C_6$-alkenyl group, an optionally substituted aryl group, an optionally substituted heteroaryl group, an aryl-$C_1$–$C_6$-alkyl group, a $C_1$–$C_6$-hydroxyalkyl group, a $C_2$–$C_6$-polyhydroxyalkyl group, a $C_1$–$C_6$-sulfoalkyl group, a $C_1$–$C_6$-carboxyalkyl group, a group $R^{III}R^{IV}N$—$(CH_2)_{q}$-, in which $R^{III}$ and $R^{IV}$, independently of one another, are a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group and q is a number 1, 2, 3 or 4,
- A is an oxygen atom, a sulfur atom or a group N—R, in which R is a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group, $X^-$ is a physiologically compatible anion,
- $R^{22}$ is a group according to formula IX,

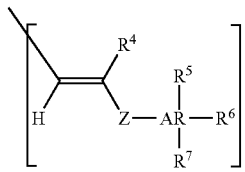
(IX)

in which
- $R^4$, $R^5$ and $R^6$, independently of one another, are a hydrogen atom, a halogen atom, a $C_1$–$C_6$-alkyl group, $C_1$–$C_6$-alkoxy group, $C_1$–$C_6$-aminoalkyl group, $C_1$–$C_6$-hydroxyalkyl group, a $C_1$–$C_6$-alkoxy-$C_1$–$C_6$-alkyloxy group, a $C_2$–$C_6$-acyl group, an acetyl group, carboxyl group, carboxylato group, carbamoyl group, sulfo group, sulfato group, sulfonamide group, sulfonamido group, $C_2$–$C_6$-alkenyl group, an aryl group, an aryl-$C_1$–$C_6$-alkyl group, a hydroxy group, a nitro group, a pyrrolidino group, a morpholino group, a piperidino group, an amino group or ammonio group or a 1-imidazol(in)io group, where the last three groups can be substituted by one or more $C_1$–$C_6$-alkyl groups, $C_1$–$C_6$-carboxyalkyl groups, $C_1$–$C_6$-hydroxyalkyl groups, $C_2$–$C_6$-alkenyl groups, $C_1$–$C_6$-alkoxy-$C_1$–$C_6$-alkyl groups, by optionally substituted benzyl groups, by sulfo -($C_1$–$C_4$)-alkyl groups or heterocycle-($C_1$–$C_4$)-alkyl groups, where two of the radicals from $R^4$, $R^5$, $R^6$ and -Z-Y—$R^3$, together with the remainder of the radical, can also form a fused-on optionally substituted 5-, 6- or 7-membered ring, which can likewise carry a fused-on aromatic ring, where the system AR can, depending on the size of the ring, carry further substituents which, independently of one another, can be the same groups as $R^4$, $R^5$ and $R^6$, $R^7$ is a hydrogen atom, a hydroxy group, a $C_1$–$C_4$-alkoxy group, a $C_1$–$C_6$-alkyl group, a $C_1$–$C_6$-hydroxyalkyl group, a $C_2$–$C_6$-polyhydroxyalkyl group, a $C_1$–$C_6$-alkoxy-$C_1$–$C_6$-alkyl group,

- AR is benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, cinnoline, acridine, julolidine, acenaphthene, fluorene, biphenyl, diphenylmethane, benzophenone, diphenyl ether, azobenzene, chromone, coumarin, diphenylamine, stilbene, where the N-heteroaromatics may also be quaternized,
- Z is a direct bond, a carbonyl group, a carboxy-($C_1$–$C_4$)-alkylene group, an optionally substituted $C_2$–$C_6$-alkenylene group, $C_4$–$C_6$-alkadienylene group, furylene group, thienylene group, arylene group, vinylenearylene group, vinylenefurylene group, vinylenethienylene group, where Z, together with the —Y—$R^3$ group, can also form an optionally substituted 5-, 6- or 7-membered ring.

17. An agent for coloring fibers containing keratin, in particular, human hair, comprising, as direct dye, at least one reaction product RP according to formula VIII,

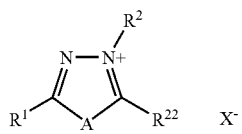
(VIII)

in which
- $R^1$ is a hydrogen atom, a hydroxy group, a mercapto group, a linear or cyclic $C_1$–$C_6$-alkyl group, a $C_2$–$C_6$-alkenyl group, an optionally substituted aryl group, an optionally substituted heteroaryl group, an aryl-$C_1$–$C_6$-alkyl group, a $C_1$–$C_6$-hydroxyalkyl group, a $C_2$–$C_6$-polyhydroxyalkyl group, a $C_1$–$C_6$-alkoxy-$C_2$–$C_6$-alkyl group, a $C_1$–$C_6$-sulfoalkyl group, a $C_1$–$C_6$-carboxyalkyl group, a group $R^IR^{II}N$—$(CH_2)_{m}$-, in which $R^I$ and $R^{II}$, independently of one another, are a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_4$ alkyl group, where $R^I$ and $R^{II}$, together with the nitrogen atom, can form a 5-, 6- or 7-membered ring and m is a number 0, 1, 2, 3 or 4,
- $R^2$ is a linear or cyclic $C_1$–$C_6$-alkyl group, a $C_2$–$C_6$-alkenyl group, an optionally substituted aryl group, an optionally substituted heteroaryl group, an aryl-$C_1$–$C_6$- alkyl group, a $C_1$–$C_6$-hydroxyalkyl group, a $C_2$–$C_6$-polyhydroxyalkyl group, a $C_1$–$C_6$-sulfoalkyl group, a $C_1$–$C_6$-carboxyalkyl group, a group $R^{III}R^{IV}N$—$(CH_2)_q$-, in which $R^{III}$ and $R^{IV}$, independently of one another, are a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group and q is a number 1, 2, 3 or 4, A is an oxygen atom, a sulfur atom or a group N—R, in which R is a hydrogen atom, a linear or cyclic $C_1$–$C_6$-alkyl group, a $C_2$–$C_6$-alkenyl group, a $C_1$–$C_6$-hydroxyalkyl group or an aryl-$C_1$–$C_6$-alkyl group, $X^-$ is a physiologically compatible anion, $R^{22}$ is a group according to formula IX,

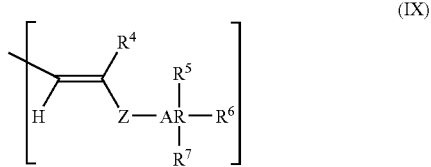

(IX)

in which $R^4$, $R^5$ and $R^6$, independently of one another, are a hydrogen atom, a halogen atom, a $C_1$–$C_6$-alkyl group, $C_1$–$C_6$-alkoxy group, $C_1$–$C_6$-aminoalkyl group, $C_1$–$C_6$-hydroxyalkyl group, a $C_1$–$C_6$-alkoxy-$C_1$–$C_6$-alkyloxy group, a $C_2$–$C_6$-acyl group, an acetyl group, carboxyl group, carboxylato group, carbamoyl group, sulfo group, sulfato group, sulfonamide group, sulfonamido group, $C_2$–$C_6$-alkenyl group, an aryl group, an aryl-$C_1$–$C_6$-alkyl group, a hydroxy group, a nitro group, a pyrrolidino group, a morpholino group, a piperidino group, an amino group or ammonio group or a 1-imidazol(in)io group, where the last three groups can be substituted by one or more $C_1$–$C_6$-alkyl groups, $C_1$–$C_6$-carboxyalkyl groups, $C_1$–$C_6$-hydroxyalkyl groups, $C_2$–$C_6$-alkenyl groups, $C_1$–$C_6$-alkoxy-$C_1$–$C_6$-alkyl groups, by optionally substituted benzyl groups, by sulfo -($C_1$–$C_4$)-alkyl groups or heterocycle-($C_1$–$C_4$)-alkyl groups, where two of the radicals from $R^4$, $R^5$, $R^6$ and -Z-Y—$R^3$, together with the remainder of the radical, can also form a fused-on optionally substituted 5-, 6- or 7-membered ring, which can likewise carry a fused-on aromatic ring, where the system AR can, depending on the size of the ring, carry further substituents which, independently of one another, can be the same groups as $R^4$, $R^5$ and $R^6$, $R^7$ is a hydrogen atom, a hydroxy group, a $C_1$–$C_4$-alkoxy group, a $C_1$–$C_6$-alkyl group, a $C_1$–$C_6$-hydroxyalkyl group, a $C_2$–$C_6$-polyhydroxyalkyl group, a $C_1$–$C_6$-alkoxy-$C_1$–$C_6$-alkyl group, AR is benzene, naphthalene, pyridine, pyrimidine, pyrazine, pyridazine, carbazole, pyrrole, pyrazole, furan, thiophene, 1,2,3-triazine, 1,3,5-triazine, quinoline, isoquinoline, indole, indoline, indolizine, indane, imidazole, 1,2,4-triazole, 1,2,3-triazole, tetrazole, benzimidazole, 1,3-thiazole, benzothiazole, indazole, benzoxazole, quinoxaline, quinazoline, quinolizine, cinnoline, acridine, julolidine, acenaphthene, fluorene, biphenyl, diphenylmethane, benzophenone, diphenyl ether, azobenzene, chromone, coumarin, diphenylamine, stilbene, where the N-heteroaromatics may also be quaternized, Z is a direct bond, a carbonyl group, a carboxy-($C_1$–$C_4$)-alkylene group, an optionally substituted $C_2$–$C_6$-alkenylene group, $C_4$–$C_6$-alkadienylene group, furylene group, thienylene group, arylene group, vinylenearylene group, vinylenefurylene group, vinylenethienylene group, where Z, together with the —Y—$R^3$ group, can also form an optionally substituted 5-, 6- or 7-membered ring.

18. The agent claimed in claim 16, characterized in that AR according to formula IX is selected from the group consisting of benzene and naphthalene.

19. The agent as claimed in claim 16, characterized in that Z according to formula IX is a direct bond or vinylene.

20. The agent claimed in claim 16, characterized in that $R^4$ according to formula IX is a hydrogen atom.

21. A colorant comprising the agent claimed in claim 16, characterized in that the reaction product RP is present in an amount of from 0.03 to 65 mmol, based on 100 g of the total colorant.

22. The agent claimed in claim 1, characterized in that the agent comprises color enhancers selected from the group consisting of piperidine, piperidine-2-carboxylic acid, piperidine-3-carboxylic acid, piperidine-4-carboxylic acid, pyridine, 2-hydroxypyridine, 3-hydroxypyridine, 4-hydroxypyridine, imidazole, 1-methylmidazole, arginine, histidine, pyrrolidine, proline, pyrrolidone, pyrrolidone-5-carboxylic acid, pyrazole, 1,2,4-triazole, piperazidine and any mixtures thereof.

23. A colorant comprising the agent claimed in claim 1, characterized in that the agent further comprises at least one direct dye, in an amount of from 0.01 to 20% by weight, based on the total colorant.

24. The agent as claimed in claims 1, characterized in that the agent further comprises at least one developer component and optionally at least one coupler component as oxidation dye precursor.

25. The agent as claimed in claim 1, characterized in that the agent further comprises ammonium salts or metal salts that are selected from the group consisting of formiates, carbonates, halides, sulfates, butyrates, valeriates, capronates, acetates, lactates, glycolates, tartrates, citrates, gluconates, propionates, phosphates and phosphonates of alkali metals, including potassium, sodium or lithium, alkaline earth metals, including magnesium, calcium, strontium, barium, aluminum, manganese, iron, cobalt, copper and zinc.

26. The agent as claimed in claim 1, characterized in that the agent contains hydrogen peroxide or other oxidizing agents or mixtures of two or more oxidizing agents.

27. The agent as claimed in claim 1, characterized in that the agent further comprises anionic, zwitterionic or nonionic surfactants.

28. A coloring component in hair colorant comprising at least one compound according to formula I in claim 1, in combination with at least one compound of component B in claim 1.

29. A method of coloring fibers containing keratin in which a composition comprising the agent of claim 1 is applied to the fibers containing keratin, left on the fibers for a certain time and then rinsed out or washed out using a shampoo.

30. The method as claimed in claim 29, characterized in that, in a two-step method, before or after application of the compound according to formula I, component B is applied to the fibers containing keratin, the mixture obtained on the hair is left on the fibers for a certain time and is then rinsed out or washed out using a shampoo.

31. The method as claimed in claim 29, characterized in that, before a colorant as in claim 1 is applied, the fibers containing keratin have been bleached in the course of a pretreatment with a bleaching agent.

32. A process for the nuancing of oxidation colorations of fibers containing keratin comprising the step of applying to the fibers containing keratin at least one compound according to formula I and/or enamine form thereof,

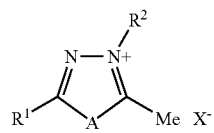

(I)

where $R^1$, $R^2$, A and $X^-$ are as defined in claim 1, in combination with reactive carbonyl compounds (component B).

33. A process for freshening up the color of human hair colored using oxidative colorants comprising the step of applying to the human hair at least one compound according to formula I and/or enamine form thereof,

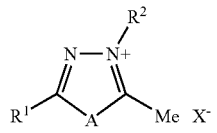

(I)

where $R^1$, $R^2$, A and $X^-$ are as defined in claim 1, in combination with reactive carbonyl compounds (component B).

* * * * *